United States Patent
Nakajima

(10) Patent No.: US 12,048,528 B2
(45) Date of Patent: Jul. 30, 2024

(54) ANNOTATION METHOD, ANNOTATION DEVICE, STORAGE MEDIUM, AND IDENTIFICATION SYSTEM

(71) Applicant: OMRON Corporation, Kyoto (JP)

(72) Inventor: Hiroshi Nakajima, Kyoto (JP)

(73) Assignee: OMRON Corporation, Kyoto (JP)

( * ) Notice: Subject to any disclaimer, the term of this patent is extended or adjusted under 35 U.S.C. 154(b) by 916 days.

(21) Appl. No.: 16/969,971

(22) PCT Filed: Mar. 13, 2019

(86) PCT No.: PCT/JP2019/010181
§ 371 (c)(1),
(2) Date: Aug. 13, 2020

(87) PCT Pub. No.: WO2019/176991
PCT Pub. Date: Sep. 19, 2019

(65) Prior Publication Data
US 2020/0397346 A1    Dec. 24, 2020

(30) Foreign Application Priority Data
Mar. 13, 2018    (JP) ................. 2018-045861

(51) Int. Cl.
*G06N 3/08* (2023.01)
*A61B 5/11* (2006.01)
*A61B 5/16* (2006.01)

(52) U.S. Cl.
CPC ............ *A61B 5/1126* (2013.01); *A61B 5/165* (2013.01); *A61B 5/167* (2013.01); *G06N 3/08* (2013.01)

(58) Field of Classification Search
CPC ....... A61B 5/1126; A61B 5/165; A61B 5/167; A61B 5/7267; G06N 3/08
See application file for complete search history.

(56) References Cited

U.S. PATENT DOCUMENTS

2007/0011206 A1*    1/2007    Gupta ............... G06F 40/169

FOREIGN PATENT DOCUMENTS

| CN | 102282516 | 12/2011 |
| CN | 107689027 | 2/2018 |

(Continued)

OTHER PUBLICATIONS

"International Search Report (Form PCT/ISA/210) of PCT/JP2019/010181", mailed on May 28, 2019, with English translation thereof, pp. 1-4.

(Continued)

*Primary Examiner* — Carl H Layno
*Assistant Examiner* — Aya Ziad Bakkar
(74) *Attorney, Agent, or Firm* — JCIPRNET

(57) ABSTRACT

An annotation method, an annotation device, a storage medium, and an identification system are provided. In an annotation method according to an aspect of the present invention, a computer executes: a step of acquiring sensor data in which the outputs of a sensor are arrayed in time series; and a step for providing a plurality of labels to the acquired sensor data. The plurality of labels include a first label and a second label, wherein the first label is provided to a first time segment, and the second label is provided to a second time segment that comes after the first time segment in the time series. In addition, the first time segment and the second time segment are set to have an overlapping segment in which the first time segment and the second time segment partially overlap each other in the time series.

12 Claims, 16 Drawing Sheets

(56) References Cited

FOREIGN PATENT DOCUMENTS

| JP | 2007142750 | | | 6/2007 | | |
|---|---|---|---|---|---|---|
| JP | 2007142750 | A | * | 6/2007 | ....... | G06F 17/30817 |
| JP | 2010191556 | | | 9/2010 | | |
| JP | 2010207488 | | | 9/2010 | | |
| JP | 2010207488 | A | * | 9/2010 | | |
| JP | 2010227326 | | | 10/2010 | | |
| JP | 2012248017 | | | 12/2012 | | |
| JP | 2017228091 | | | 12/2017 | | |
| WO | 2017037839 | | | 3/2017 | | |

OTHER PUBLICATIONS

"Written Opinion of the International Searching Authority (Form PCT/ISA/237) of PCT/JP2019/010181", mailed on May 28, 2019, with English translation thereof, pp. 1-8.
Tanaka, Yusuke et al., "Simple Annotation Method for Time-Series Driving Behavior Data", 2th volume of Lecture proceedings of 13th Forum on Information Technology (FIT) Aug. 19, 2014, pp. 67-70.
Office Action of China Counterpart Application, with English translation thereof, issued on May 18, 2023, pp. 1-18.
"Office Action of Japan Counterpart Application", issued on Nov. 10, 2020, with English translation thereof, p. 1-p. 6.

* cited by examiner

ANNOTATION METHOD, ANNOTATION DEVICE, STORAGE MEDIUM, AND IDENTIFICATION SYSTEM

BACKGROUND

Technical Field

The present invention relates to an annotation method, an annotation device, a storage medium, and an identification system.

Related Art

Conventionally, annotation processing is performed to assign a label to target data in various situations. For example, annotation processing may be performed on each part of video data to show the content of each part of the video data. In addition, for example, in Patent literature 1, a method has been proposed in which sensor data obtained from an acceleration sensor, and labels assigned to the sensor data and indicating the type of behavior represented by the sensor data are used to learn the behavior model of a user. The label indicates some information of the data in the assigned time segment, and is used for various purposes such as correct answer data (teacher data) in supervised learning as in Patent literature 1 for example.

LITERATURE OF PRIOR ART

Patent Literature

Patent literature 1: Japanese Patent Laid-Open No. 2012-248017

SUMMARY

Problems to be Solved

Conventionally, when annotating sensor data in which the outputs of a sensor are continuously arranged in time series, the sensor data is divided into time segments and a label is assigned to each of the obtained time segments. However, the present inventor has found that the above annotation method has the following problems.

That is, in the sensor data, the outputs of the sensor are arranged continuously, and a certain state indicated by a certain time segment gradually transits to another state indicated by the next time segment, thus making it difficult to correctly determine the boundary time of each time segment. In addition, for the same reason, the content of the label assigned at the boundary of each time segment may not be uniquely determined. The present inventor has found that in the conventional annotation method, it is difficult to accurately add desired information to sensor data due to the above reasons.

For example, assume that labels indicating the behavioral state of a user such as walking (walking state), sitting on a chair (sitting state), and standing up from the chair (standing state) are assigned to the sensor data obtained from an acceleration sensor worn by the user. In this case, when the user takes an action to change the behavioral state, such as transitioning from the walking state to the sitting state or transitioning from the sitting state to the standing state, the timing at which the behavioral state is switched is ambiguous, thus making it difficult to correctly determine the time when the behavioral state is switched. In addition, it is unclear whether a label indicating the behavioral state before the transition or a label indicating the behavioral state after the transition should be assigned to the segment where each behavioral state is transitioning. Accordingly, it is difficult to uniquely determine the content of the label assigned to the segment where each behavioral state is transitioning. Therefore, in this case, it is difficult to accurately add information indicating the behavioral state of the user to the sensor data in the conventional annotation method.

One aspect of the present invention has been made in view of the above circumstances, and an objective of the present invention is to provide an annotation technology which can add desired information to sensor data more accurately.

Means to Solve Problems

The present invention adopts the following configurations to solve the above-mentioned problems.

That is, in the annotation method according to one aspect of the present invention, a computer executes: a step of acquiring sensor data in which the outputs of a sensor are arranged in time series; and a step of assigning a plurality of labels to the acquired sensor data. The plurality of labels include a first label and a second label, the first label is assigned to a first time segment, and the second label is assigned to a second time segment that comes after the first time segment in the time series. Then, the start time of the first time segment is earlier than the start time of the second time segment, and the end time of the first time segment is earlier than the end time of the second time segment, whereas the end time of the first time segment is later than the start time of the second time segment, and thereby the first time segment and the second time segment are set to have an overlapping segment in which the first time segment and the second time segment partially overlap each other in the time series.

In the annotation method, when the plurality of labels are assigned to the sensor data, an overlapping segment is arranged between the first time segment assigned with the first label and the second time segment assigned with the second label and coming after the first time segment, in which the first time segment and the second time segment partially overlapping each other in the time series in the overlapping segment. Accordingly, the boundary between the first time segment and the second time segment can have a temporal width, and the timing of the transition from the state indicated by the first label to the state indicated by the second label may not be determined at one point. That is, when the timing of the transition from the state of the first label to the state of the second label is unknown, the transition can occur at any time (timing) in the overlapping segment, or the overlapping segment can be used as the segment in which the transition occurs. Consequently, according to the annotation method, the segment in which state transition occurs can be appropriately represented by the overlapping segment, and thus compared with the conventional method in which the boundary of the time segment is determined at one point, desired information can be added to the sensor data more accurately.

Moreover, the type of the "sensor" is not particularly limited as long as it can acquire some data in time series, and the sensor may be appropriately selected according to the embodiment. The "sensor" may be, for example, a biosensor (a sensor capable of measuring heartbeat, body temperature, myoelectricity, electrocardiogram, brain wave, and the like), an activity sensor (a sensor capable of measuring vibration, acceleration, and the like), a motion sensor, a camera, a microphone, a load cell, and the like.

The "sensor data" is the data in which the outputs of a sensor are arranged in time series on the time axis, and the type of the sensor data may be appropriately determined according to the type of the sensor. The "sensor data" may be, for example, at least any one of numerical data, text data, image data, and audio data. Additionally, because the outputs of the sensor are arranged in time series, the "sensor data" may also be referred to as "time series data".

The "label" provides some information to a target time segment in the sensor data, and the content of the label may be appropriately determined according to the embodiment. The label may be set to indicate, for example, the content, characteristics, and the like of the data in the target time segment. The label may be used for information processing such as machine learning. When the "label" can be used for supervised learning, the "label" may also be referred to as "teacher data" or "correct answer data". In this case, the content of the label may be the correct answer of an inference that a learner acquires by the supervised learning. Moreover, hereinafter, the sensor data assigned with a plurality of labels is also referred to as "labelled sensor data".

In the annotation method according to the above aspect, the computer may set a boundary time that provisionally divides the first time segment and the second time segment, and set the overlapping segment having a predetermined time width so as to include at least one time before or after the set boundary time. According to this method, the overlapping segment can be easily set on the basis of the provisional boundary time, and thus the cost of annotation can be reduced.

In the annotation method according to the above aspect, the predetermined time width may be determined based on the type of at least one of the first label and the second label. According to this method, the overlapping segment can be appropriately set based on the type of the label to be assigned, and thus desired information can be added to the sensor data more accurately. Moreover, the specific value of the time width of the overlapping segment corresponding to the type of the label may be appropriately determined according to the embodiment. For example, a scene in which actions of "visually recognizing", "holding", "transporting", and "adjusting" taken by a factory worker are monitored by a sensor is assumed. In this scene, it is assumed that compared with the transition from the "holding" state to the "transporting" state, the time required for the transition from the "visually recognizing" state to the "holding" state is usually longer. Consequently, in this scene, the time width of the overlapping segment between the time segment labelled with "visually recognizing" and the time segment labelled with "holding" may be set to be longer than the time width of the overlapping segment between the time segment labelled with "holding" and the time segment labelled with "transporting".

In the annotation method according to the above aspect, the predetermined time width may be a fixed value. According to this method, the amount of calculation required to set the overlapping segment can be reduced, and thus the cost of annotation can be reduced.

In the annotation method according to the above aspect, the computer may receive a designation of time from a user and set the designated time as the boundary time. According to this method, the boundary time that serves as the basis of the overlapping segment can be set by a simple method, and thus the cost of annotation can be reduced.

In the annotation method according to the above aspect, the computer may receive a plurality of designations for the boundary time that provisionally divides the first time segment and the second time segment, and may set the overlapping segment based on at least any one of an average and a variation of the boundary times given by the plurality of designations. According to this method, the overlapping segment can be appropriately set based on at least any one of the average and the variation of the boundary times given by the plurality of designations, and thus desired information can be added to the sensor data more accurately.

In the annotation method according to the above aspect, the computer may receive a designation of a segment in which the first time segment and the second time segment overlap, and may set the designated segment as the overlapping segment. According to this method, the overlapping segment can be easily set, and thus the cost of annotation can be reduced.

In the annotation method according to the above aspect, the computer may set the time width of the overlapping segment based on a sampling cycle of the sensor by including a plurality of sample points for sampling the outputs of the sensor respectively in the overlapping segment. According to this method, the overlapping segment is set to include a plurality of sample points. This prevents the overlapping segment from being set to contain substantially only one time point and ensures that the boundary between the first time segment and the second time segment have a temporal width.

In the annotation method according to the above aspect, the computer may assign a first value as the first label to a segment from the start time of the first time segment to the start time of the second time segment, may assign a second value as the second label to a segment from the end time of the first time segment to the end time of the second time segment, and may assign one or more values as the labels of the overlapping segment to a segment from the end time of the first time segment to the start time of the second time segment so as to transition from the first value to the second value. According to this method, a label indicating a state of transitioning from the state indicated by the first label to the state indicated by the second label is assigned to the overlapping segment, and thereby desired information can be added to the sensor data more accurately. Moreover, when the content of the label assigned to the overlapping segment is different from the content of the first label and the second label, the label assigned to the overlapping segment may be referred to as a "third label" to distinguish it from the first label and the second label.

In the annotation method according to the above aspect, each of the plurality of labels may be set to indicate the correct answer of a predetermined inference on the sensor data in a time segment to which the label is assigned. According to this method, the labelled sensor data available for the supervised learning can be generated.

In the annotation method according to the above aspect, the computer may further execute: a step of acquiring evaluation result data indicating the evaluation result of a trained learner which is constructed to have the ability to perform a predetermined inference by performing the supervised learning using the sensor data and the plurality of labels, and a step of changing the time width of the overlapping segment based on the evaluation result indicated by the acquired evaluation result data. When each label is appropriately assigned to the sensor data, the ability of the trained learner constructed by the supervised learning using the labelled sensor data to perform the predetermined inference is higher (that is, the evaluation on the trained learner is higher). On the other hand, when each label is not appropriately assigned to the sensor data due to inaccurate time width of the overlapping segment or other reasons, the ability of the trained learner constructed by the supervised learning using the labelled sensor data to perform the predetermined inference is lower (that is, the evaluation on the trained learner is lower). In this method, by changing the time width of the overlapping segment, each labelled time segment is adjusted, and the labels can be appropriately assigned to the time segments of the sensor data. Consequently, according to this method, labelled sensor data capable of constructing a trained learner having a high ability to perform a predetermined inference can be generated. Moreover, the "trained learner" may be referred to as an "identifier" or a "classifier".

In the annotation method according to the above aspect, the evaluation result may be represented by a correct answer rate at a time when a predetermined inference is performed on other sensor data different from the above sensor data by the trained learner. When the correct answer rate indicated by the evaluation result data is less than or equal to a predetermined threshold, the computer may change the time width of the overlapping segment by narrowing or expanding the time width of the overlapping segment. According to this method, labelled sensor data capable of constructing a trained learner having an ability above a certain level to perform a predetermined inference can be generated.

Moreover, as another embodiment of the annotation method according to above embodiments, one aspect of the present invention may be an information processing device capable of executing the above steps, a program, or a storage medium that stores such a program and is readable by a computer, other devices, machines, or the like. Here, the storage medium readable by a computer and the like is a medium for storing information, such as a program, by electrical, magnetic, optical, mechanical, or chemical action.

For example, the annotation device according to one aspect of the present invention is an information processing device including a data acquisition unit for acquiring sensor data in which the outputs of a sensor are arranged in time series, and a label assignment unit for assigning a plurality of labels to the acquired sensor data. The plurality of labels include a first label and a second label, the first label is assigned to a first time segment, and the second label is assigned to a second time segment that comes after the first time segment in the time series. The start time of the first time segment is earlier than the start time of the second time segment, and the end time of the first time segment is earlier than the end time of the second time segment, whereas the end time of the first time segment is later than the start time of the second time segment, and thereby the first time segment and the second time segment are set to have an overlapping segment in which the first time segment and the second time segment partially overlap each other in the time series.

In addition, for example, the non-transitory computer readable storage medium according to one aspect of the present invention stores an annotation program for causing a computer to execute: a step of acquiring sensor data in which the outputs of a sensor are arranged in time series, and a step of assigning a plurality of labels to the acquired sensor data. The plurality of labels include a first label and a second label, the first label is assigned to a first time segment, and the second label is assigned to the second time segment that comes after the first time segment in time series. The start time of the first time segment is earlier than the start time of the second time segment, the end time of the first time segment is earlier than the end time of the second time segment, whereas the end time of the first time segment is later than the start time of the second time segment, and thereby the first time segment and the second time segment are set to have an overlapping segment in which the first time segment and the second time segment partially overlap each other in the time series.

In addition, a system for performing a predetermined inference by using the trained learner constructed by the supervised learning using the sensor data and the plurality of labels, an information processing device, an information processing method, a program, a storage medium that stores such a program and is readable by a computer, other devices, machines, or the like may be configured.

For example, an identification system according to one aspect of the present invention includes: a data acquisition unit for acquiring sensor data in which the outputs of a sensor for monitoring the behavioral state of a factory worker are arranged in time series; a label assignment unit for assigning a plurality of labels to the acquired sensor data, each of the plurality of labels being set to indicate a correct answer of the behavioral state of the worker represented by the sensor data in a time segment to which the label is assigned; a learning processing unit for constructing a trained learner to have the ability to estimate the type of the behavioral state of the worker by performing supervised learning using the sensor data and the plurality of labels; a target data acquisition unit for acquiring target sensor data being a target from which the behavioral state of the worker is estimated; a state estimation unit for estimating the behavioral state of the worker represented by the target sensor data by inputting the target sensor data to the trained learner and obtaining an output from the trained learner; and an output unit for outputting the result of estimating the behavioral state of the worker. The plurality of labels include a first label and a second label, the first label is assigned to the first time segment, and the second label is assigned to a second time segment that comes after the first time segment in the time series. The start time of the first time segment is earlier than the start time of the second time segment, and the end time of the first time segment is earlier than the end time of the second time segment, whereas the end time of the first time segment is later than the start time of the second time segment, and thereby the first time segment and the second time segment are set to have an overlapping segment in which the first time segment and the second time segment partially overlap each other in the time series.

In addition, for example, the identification system according to one aspect of the present invention includes: a data acquisition unit for acquiring sensor data in which the outputs of a sensor are arranged in time series; a label assignment unit for assigning a plurality of labels to the acquired sensor data, each of the plurality of labels being set to indicate a correct answer of a predetermined inference on the sensor data in a time segment to which the label is assigned; a learning processing unit for constructing a trained learner to have the ability to perform the predetermined inference by performing supervised learning using the sensor data and the plurality of labels; a target data acquisition unit for acquiring target sensor data being a target on which the predetermined inference is performed; an inference unit for performing the predetermined inference on the target sensor data by inputting the target sensor data to the trained learner and obtaining an output from the trained learner; and an output unit for outputting a result of performing the predetermined inference. The plurality of labels include a first label and a second label, the first label is assigned to the first time segment, and the second label is assigned to a second time segment that comes after the first time segment in the time series. The start time of the first time segment is earlier than the start time of the second time segment, and the end time of the first time segment is earlier than the end time of the second time segment, whereas the end time of the first time segment is later than the start time of the second time segment, and thereby the first time segment and the second time segment are set to have an overlapping segment in which the first time segment and the second time segment partially overlap each other in the time series.

Effect

According to the present invention, an annotation technology which can add desired information to sensor data more accurately can be provided.

DESCRIPTION OF THE EMBODIMENTS

Hereinafter, an embodiment according to one aspect of the present invention (hereinafter, also referred to as "the present embodiment") is described with reference to the drawings. However, the present embodiment described below is merely an example of the present invention in all respects. It is evident that various improvements and modifications can be made without departing from the scope of the present invention. That is, in implementing the present invention, a specific configuration according to the embodiment may be appropriately adopted. Moreover, the data appears in the embodiment is described in natural language, more specifically, the data is specified by a computer-recognizable pseudo language, command, parameter, machine language, or the like.

§ 1 Application Example

Figure 1:
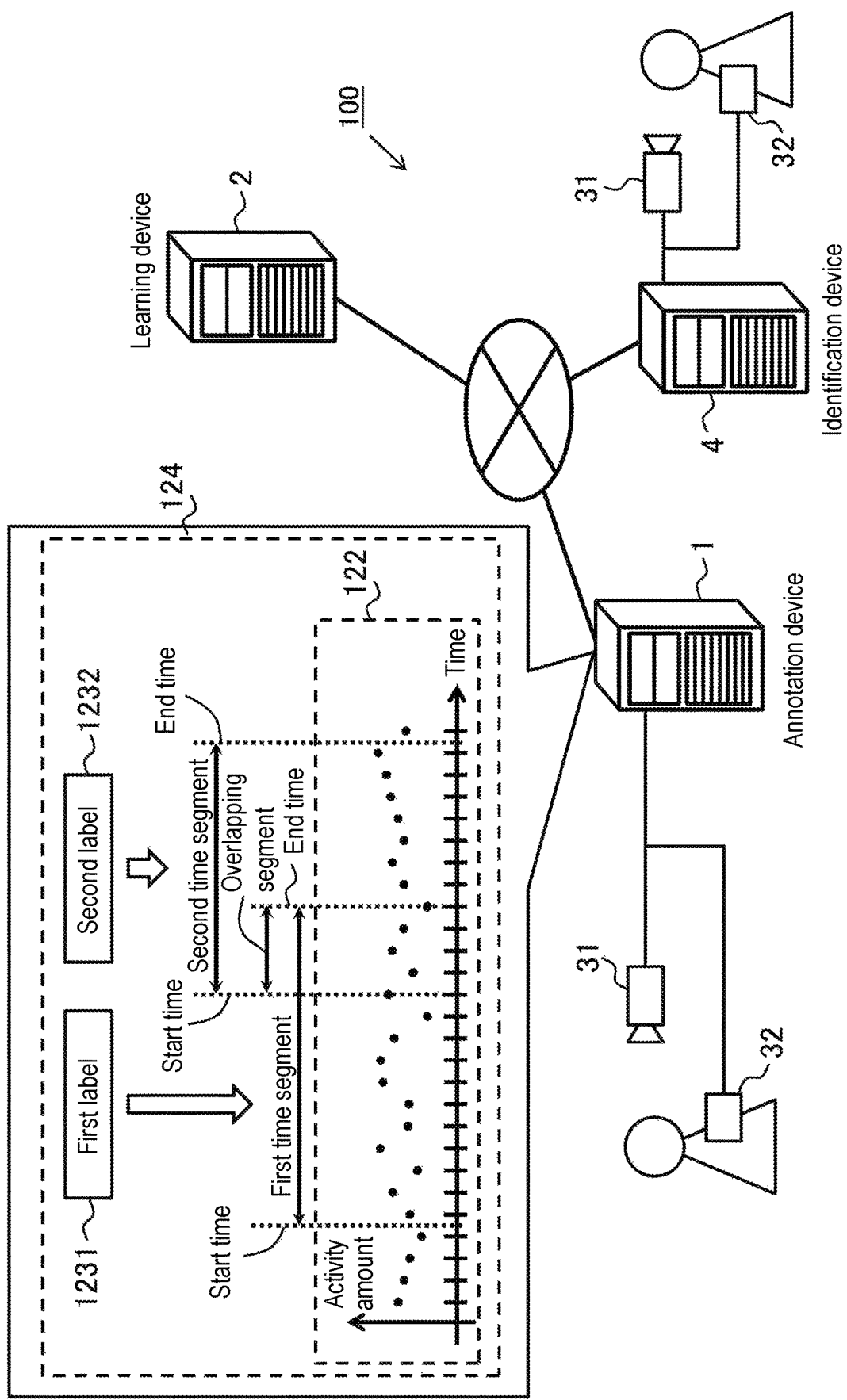
FIG. 1 schematically illustrates an example of a scene to which the present invention is applied.

First, an example of a scene to which the present invention is applied is described with reference to FIG. 1. FIG. 1 schematically illustrates an example of an application scene of an identification system 100 according to the present embodiment. The identification system 100 according to the present embodiment is a system for monitoring the behavioral state of a factory worker and is configured with an annotation device 1, a learning device 2, and an identification device 4 which are connected to each other via a network.

The annotation device 1 is an information processing device for acquiring sensor data in which the outputs of a sensor are arranged in time series and assigning a plurality of labels to the acquired sensor data. The type of the sensor is not particularly limited as long as it can acquire some data in time series, and the sensor may be appropriately selected according to the embodiment. The sensor may be, for example, a biosensor (a sensor capable of measuring heartbeat, body temperature, myoelectricity, electrocardiogram, brain waves, and the like), an activity sensor (a sensor capable of measuring vibration, acceleration, and the like), a motion sensor, a camera, a microphone, a load cell, and the like.

In addition, the sensor data is data in which the outputs of the sensor are arranged in time series on the time axis, and the type of the sensor data may be appropriately determined according to the type of the sensor. The sensor data may be, for example, at least any one of numerical data, text data, image data, and audio data. Because the outputs of the sensor are arranged in time series, the sensor data may also be referred to as "time series data".

In the present embodiment, a camera 31 and an activity sensor 32 are used as an example of the sensor to monitor the state of a factory worker. The camera 31 may be a known image capturing device and generates image data as sensor data 122. In addition, the activity sensor 32 is, for example, an acceleration sensor and is attached to the clothes of the worker. The activity sensor 32 generates numerical data as the sensor data 122. The camera 31 and the activity sensor 32 are examples of the "sensor for monitoring the state of a factory worker" of the present invention. The annotation device 1 according to the present embodiment acquires the sensor data 122 from the camera 31 and the activity sensor 32. Moreover, in FIG. 1, only the numerical data obtained from the activity sensor 32 is illustrated as the sensor data 122 for simplification. In the present embodiment, the image data obtained from the camera 31 is also processed in the same manner as the numerical data obtained from the activity sensor 32, and the illustration thereof is omitted.

Next, the annotation device 1 according to the present embodiment generates labelled sensor data 124 by assigning a plurality of labels to the acquired sensor data 122. At this time, a plurality of time segments set in the sensor data 122 include a first time segment and a second time segment that are adjacent to each other in time series. The second time segment is set so as to continue after the first time segment in the time series. In addition, the assigned labels include a first label 1231 and a second label 1232. The first label 1231 is assigned to the first time segment, and the second label 1232 is assigned to the second time segment.

Each labelled time segment is a segment set in the time series (time axis) by the start time and the end time in the sensor data 122. In the present embodiment, the start time of the first time segment is set to be earlier than the start time of the second time segment, and the end time of the first time segment is set to be earlier than the end time of the second time segment, whereas the end time of the first time segment is set to be later than the start time of the second time segment. Accordingly, in the present embodiment, the first time segment and the second time segment are set to have an overlapping segment in which the first time segment and the second time segment partially overlap each other in the time series. This overlapping segment can be regarded as a time segment assigned with both the first label 1231 and the second label 1232 which are respectively assigned to the first time segment and the second time segment. In addition, a label different from the first label 1231 and the second label 1232 (for example, a label indicating the transition from the first label 1231 to the second label 1232) may also be assigned to this overlapping segment.

Each of the labels assigned to the time segments adds some information to a target time segment in the sensor data, and the content of the label may be appropriately determined according to the embodiment. In addition, each label may be set to indicate, for example, the content, characteristics and the like of the data in the target time segment. In the present embodiment, the content of each label is set to indicate the correct answer of a predetermined inference on the sensor data 122 in the time segment assigned with this label. Specifically, the sensor data 122 is obtained from the camera 31 and the activity sensor 32 for monitoring the state of the factory worker, so that each label is set to indicate the correct answer of the behavioral state of the worker indicated by the sensor data 122 in the labelled time segment.

Therefore, the generated labelled sensor data 124 can be used for the supervised learning which is configured to enable the learner to acquire the ability of estimating the type of the behavioral state of the worker based on the sensor data obtained from the camera and the activity sensor, as an example of the predetermined inference. Consequently, the learning device 2 according to the present embodiment acquires the labelled sensor data 124 from the annotation device 1 and uses the acquired labelled sensor data 124 to perform the supervised learning of the learner. Accordingly, the learning device 2 according to the present embodiment constructs a trained learner having the ability to estimate the type of behavioral state of the worker based on the sensor data obtained from the camera and the activity sensor.

Specifically, the learning device 2 acquires the labelled sensor data 124 from the annotation device 1 via a network or the like. Then, when the sensor data 122 in the target time segment is input, the learning device 2 trains the learner (a neural network 5 described later) to output a value corresponding to the label assigned to the time segment of the sensor data 122 that has been input. Accordingly, the learning device 2 uses the labelled sensor data 124 to construct a trained learner for estimating the type of the behavioral state of the worker based on the data obtained from the camera and the activity sensor.

Then, the identification device 4 according to the present embodiment uses the trained learner to estimate the behavioral state of the worker. That is, the identification device 4 according to the present embodiment acquires, from the camera 31 and the activity sensor 32, target sensor data being a target from which the behavioral state of the worker is estimated. Subsequently, the identification device 4 inputs the target sensor data into the trained learner to obtain an output from the trained learner, thereby estimating the behavioral state of the worker represented by the target sensor data. Then, the identification device 4 outputs the estimation result of the behavioral state of the worker.

As described above, in the annotation method according to the present embodiment, when a plurality of labels are assigned to the sensor data 122, an overlapping segment is arranged between the first time segment assigned with the first label 1231 and the second time segment assigned with the second label 1232, the first time segment and the second time segment partially overlapping each other in the time series in the overlapping segment. Accordingly, the boundary between the first time segment and the second time segment can have a temporal width, and the timing of the transition from the state indicated by the first label 1231 to the state indicated by the second label 1232 may not be determined at one point. That is, the transition from the state indicated by the first label 1231 to the state indicated by the second label 1232 occurs at any time in the overlapping segment shown in FIG. 1, or the overlapping segment can be used to represent the segment in which the transition occurs.

Therefore, according to the annotation method of the present embodiment, the overlapping segment arranged between the first time segment and the second time segment can appropriately represent the segment in which the transition from the state indicated by the first label 1231 to the state indicated by the second label 1232 occurs. Accordingly, compared with the conventional method in which the boundary of the time segment is determined at one point, desired information can be added to the sensor data 122 more accurately.

In addition, in the conventional method, if the boundary time of each time segment is set to an incorrect time, or a label indicating any state is assigned to a segment transitioning from a certain state to another state, the information added to the sensor data may be inaccurate, which may cause various adverse effects on a scene in which the label is used. For example, a scene is assumed in which the labelled sensor data obtained from the above case is used to perform, on the sensor data, supervised learning for enabling the learner to acquire the ability to perform an inference of estimating the behavioral state of a user. In this case, the time may be set as the boundary time to transition to the next behavioral state despite that the time is still in the walking state, or a label indicating the "walking state" may be assigned to a segment where the walking state is shifted to the sitting state, which may cause labelling that does not accurately reflect the behavioural state of the user. If the labelling is not performed accurately reflecting the behavioural state of the user, the label does not accurately reflect, at least in part, the behavioural state of the user. Accordingly, if the label of this part is used as correct answer data (teacher data), erroneous learning is carried out, and the performance (that is, inference ability) of the trained learner constructed by supervised learning may decrease.

On the other hand, according to the present embodiment, desired information including correct answer data can be added to the sensor data 122 more accurately. Therefore, a trained learner having a relatively high inference ability can be constructed by performing supervised learning using the labelled sensor data 124. For example, in the learning device 2 in which the labelled sensor data 124 is used for supervised learning, a trained learner having a higher ability to estimate the type of the behavioral state of the worker based on the data obtained from the camera and the activity sensor can be constructed. Accordingly, the identification device 4 can estimate the behavioral state of the worker with a high accuracy.

§ 2 Configuration Example

[Hardware Configuration]
<Annotation Device>

Figure 2:
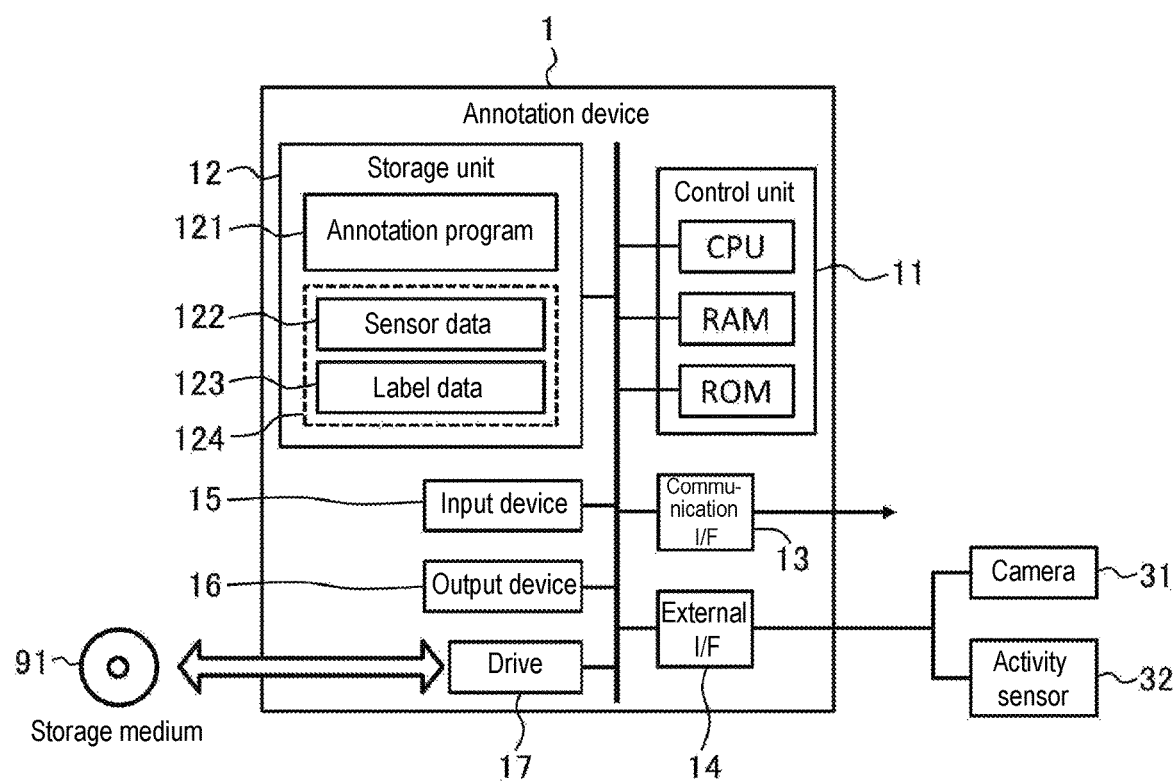
FIG. 2 schematically illustrates an example of the hardware configuration of an annotation device according to an embodiment.

Next, an example of the hardware configuration of the annotation device 1 according to the present embodiment is described with reference to FIG. 2. FIG. 2 schematically illustrates an example of the hardware configuration of the annotation device 1 according to the present embodiment.

As shown in FIG. 2, the annotation device 1 according to the present embodiment is a computer in which a control unit 11, a storage unit 12, a communication interface 13, an external interface 14, an input device 15, an output device 16, and a drive 17 are electrically connected. Moreover, in FIG. 2, the communication interface and the external interface are described as "communication I/F" and "external I/F".

The control unit 11 includes a central processing unit (CPU) being a hardware processor, a random access memory (RAM), a read only memory (ROM) and the like, and is configured to execute information processing based on the programs and various data. The storage unit 12 is an example of a memory and includes, for example, a hard disk drive, a solid state drive, or the like. In the present embodiment, the storage unit 12 stores various information such as an annotation program 121, sensor data 122, label data 123, and the like.

The annotation program 121 is a program for causing the annotation device 1 to execute the information processing (FIGS. 9 and 17) described later for acquiring the sensor data 122 and annotating the acquired sensor data 122, and includes a series of commands of the information processing. The label data 123 is data for managing a plurality of labels assigned to the sensor data 122. The labelled sensor data 124 includes the sensor data 122 and the label data 123. The details are described later.

The communication interface 13 is, for example, a wired local area network (LAN) module, a wireless LAN module, or the like, and is used for performing wired or wireless communication via a network. The annotation device 1 can perform data communication with the learning device 2 via a network by using the communication interface 13. Moreover, the type of the network between the annotation device 1 and the learning device 2 may be appropriately selected from, for example, the Internet, a wireless communication network, a mobile communication network, a telephone network, a dedicated network, and the like.

The external interface 14 is, for example, a universal serial bus (USB) port, a dedicated port, or the like, and is used for connecting to an external device. The type and the number of the external interface 14 may be appropriately selected according to the type and the number of the external device to be connected. In the present embodiment, the annotation device 1 is connected to the camera 31 and the activity sensor 32 via the external interface 14.

The camera 31 and the activity sensor 32 are examples of the "sensor" in the present invention. In order to monitor the state of the factory worker, for example, the camera 31 is arranged at a place where the image of the worker can be captured, and the activity sensor 32 is attached to the clothes of the factory worker. Moreover, when the camera 31 and the activity sensor 32 are provided with a communication interface, the annotation device 1 may be connected to the camera 31 and the activity sensor 32 via the communication interface 13 instead of the external interface 14.

The input device 15 is a device for inputting, such as a mouse, a keyboard, or the like. The output device 16 is a device for outputting, such as a display, a speaker, or the like. The labelling to the sensor data 122 may be automatically performed by the device or may be performed by operation of the user on the device. When the labelling is performed by the user, the user can assign a label to the sensor data 122 by operating the annotation device 1 using the input device 15 and the output device 16.

The drive 17 is, for example, a CD drive, a DVD drive, or the like, and is used for reading a program stored in a storage medium 91. The type of the drive 17 may be appropriately selected according to the type of the storage medium 91. At least any one of the annotation program 121 and the sensor data 122 may be stored in the storage medium 91.

The storage medium 91 is a medium for storing information, such as a program, by electrical, magnetic, optical, mechanical, or chemical action in order that the recorded information such as program can be read by a computer or other devices, machines, or the like. The annotation device 1 may acquire at least any one of the annotation program 121 and the sensor data 122 from the storage medium 91.

Here, in FIG. 2, a disc type storage medium such as a CD, a DVD, or the like is illustrated as an example of the storage medium 91. However, the type of the storage medium 91 is not limited to the disc type and may be other types. The storage medium other than the disc type may be, for example, a semiconductor memory such as a flash memory and the like.

Moreover, regarding the specific hardware configuration of the annotation device 1, constituent components can be omitted, replaced, and added as appropriate according to the embodiment. For example, the control unit 11 may include a plurality of hardware processors. The hardware processor may include a microprocessor, a field-programmable gate array (FPGA), a digital signal processor (DSP), or the like. The storage unit 12 may include a RAM and a ROM included in the control unit 11. At least any one of the communication interface 13, the external interface 14, the input device 15, and the output device 16 may be omitted. The annotation device 1 may include a plurality of computers. In this case, the hardware configuration of each computer may be the same or different. Additionally, the annotation device 1 may be a general-purpose server device, personal computer (PC), or the like, in addition to the information processing device designed specifically for the service to provide.

Learning Device

Figure 3:
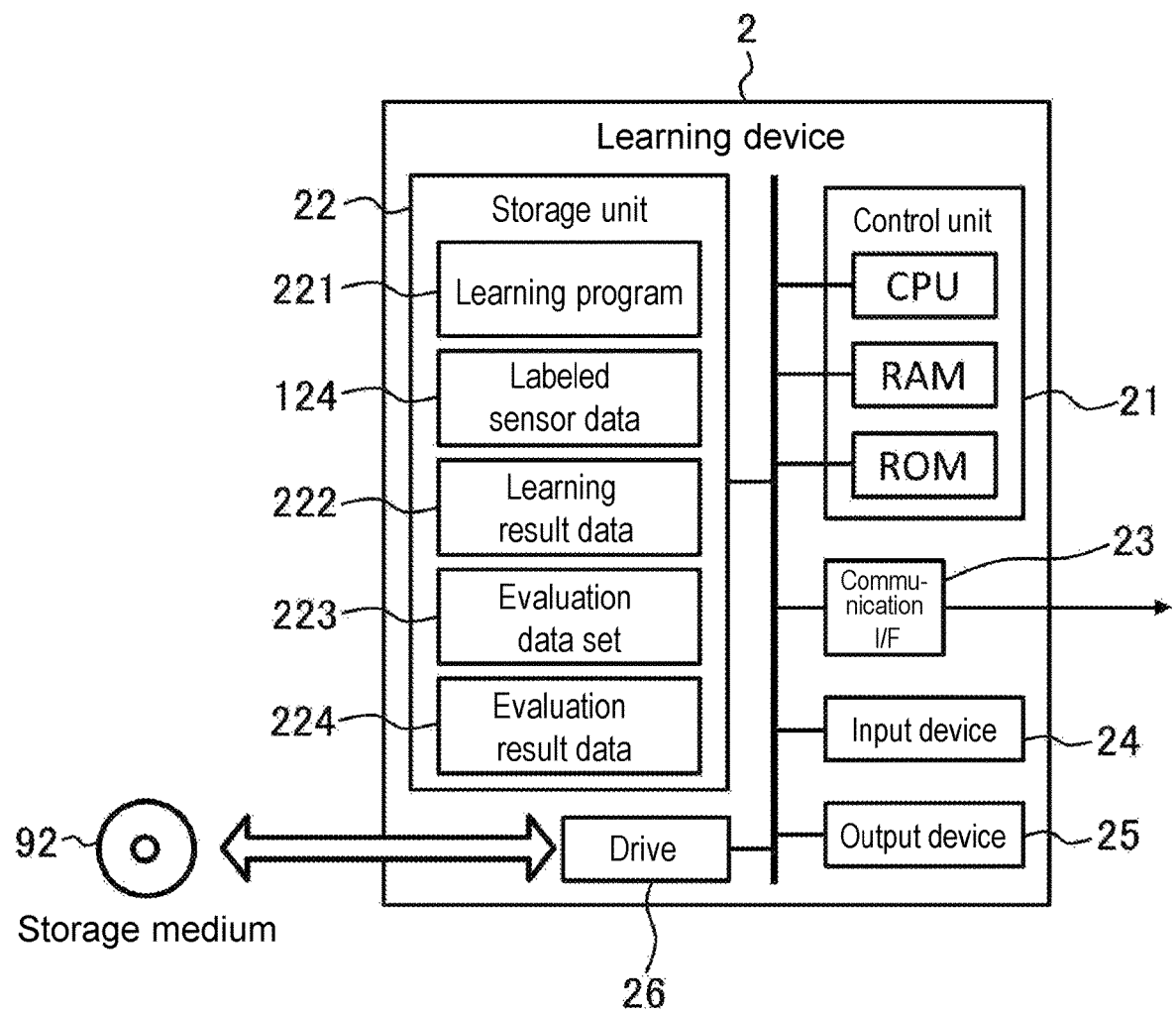
FIG. 3 schematically illustrates an example of the hardware configuration of a learning device according to an embodiment.

Next, an example of the hardware configuration of the learning device 2 according to the present embodiment is described with reference to FIG. 3. FIG. 3 schematically illustrates an example of the hardware configuration of the learning device 2 according to the present embodiment.

As shown in FIG. 3, the learning device 2 according to the present embodiment is a computer in which a control unit 21, a storage unit 22, a communication interface 23, an input device 24, an output device 25, and a drive 26 are electrically connected. Moreover, similar to FIG. 2, the communication interface in FIG. 3 is described as "communication I/F".

The control unit 21 to the drive 26, and the storage medium 92 have the same configuration as the control unit 11 to the communication interface 13, the input device 15 to the drive 17 of the annotation device 1, and the storage medium 91, respectively. The control unit 21 includes a CPU serving as a hardware processor, a RAM, a ROM, and the like, and is configured to execute various information processing based on programs and data. The storage unit 22 includes, for example, a hard disk drive, a solid state drive, or the like. The storage unit 22 is configured to store a variety of information such as a learning program 221, the labelled sensor data 124, learning result data 222, an evaluation data set 223, evaluation result data 224, and the like.

The learning program 221 is a program for causing the learning device 2 to execute the information processing of supervised learning (FIG. 16) described later for enabling the learner to acquire the ability to perform a predetermined inference by using the labelled sensor data 124, and includes a series of commands of the information processing. The learning result data 222 is data for setting the trained learner constructed by supervised learning. The evaluation data set 223 is a data set for evaluating the inference ability of the trained learner constructed by supervised learning. The evaluation result data 224 shows the result of the evaluation on the inference ability of the trained learner using the evaluation data set 223. The details are described later.

The communication interface 23 is, for example, a wired LAN module, a wireless LAN module, or the like, and is used for performing wired or wireless communication via a network. The learning device 2 can perform data communication with the annotation device 1 via a network by using the communication interface 23.

The input device 24 is a device for inputting, such as a mouse, a keyboard, or the like. The output device 25 is a device for outputting, such as a display, a speaker, or the like. An operator can operate the learning device 2 via the input device 24 and the output device 25.

The drive 26 is, for example, a CD drive, a DVD drive, or the like, and is a drive device used for reading a program stored in the storage medium 92. The type of the drive 26 may be appropriately selected according to the type of the storage medium 92. At least one of the learning program 221, the labelled sensor data 124, and the evaluation data set 223 may be stored in the storage medium 92.

The storage medium 92 is a medium for storing information, such as a program, by electrical, magnetic, optical, mechanical, or chemical action in order that the recorded information such as a program can be read by a computer or other devices, machines, or the like. The learning device 2 may acquire at least one of the learning program 221, the labelled sensor data 124, and the evaluation data set 223 from the storage medium 92.

Here, similar to FIG. 2, a disc type storage medium such as a CD, a DVD, or the like is illustrated as an example of the storage medium 92 in FIG. 3. However, similar to the storage medium 91, the type of the storage medium 92 is not limited to the disc type and may be other types.

Moreover, regarding the specific hardware configuration of the learning device 2, similar to the annotation device 1, constituent components can be omitted, replaced, and added as appropriate according to the embodiment. In addition, the learning device 2 may be a general-purpose server device, PC, or the like, in addition to the information processing device designed specifically for the service to provide.

Identification Device

Figure 4:
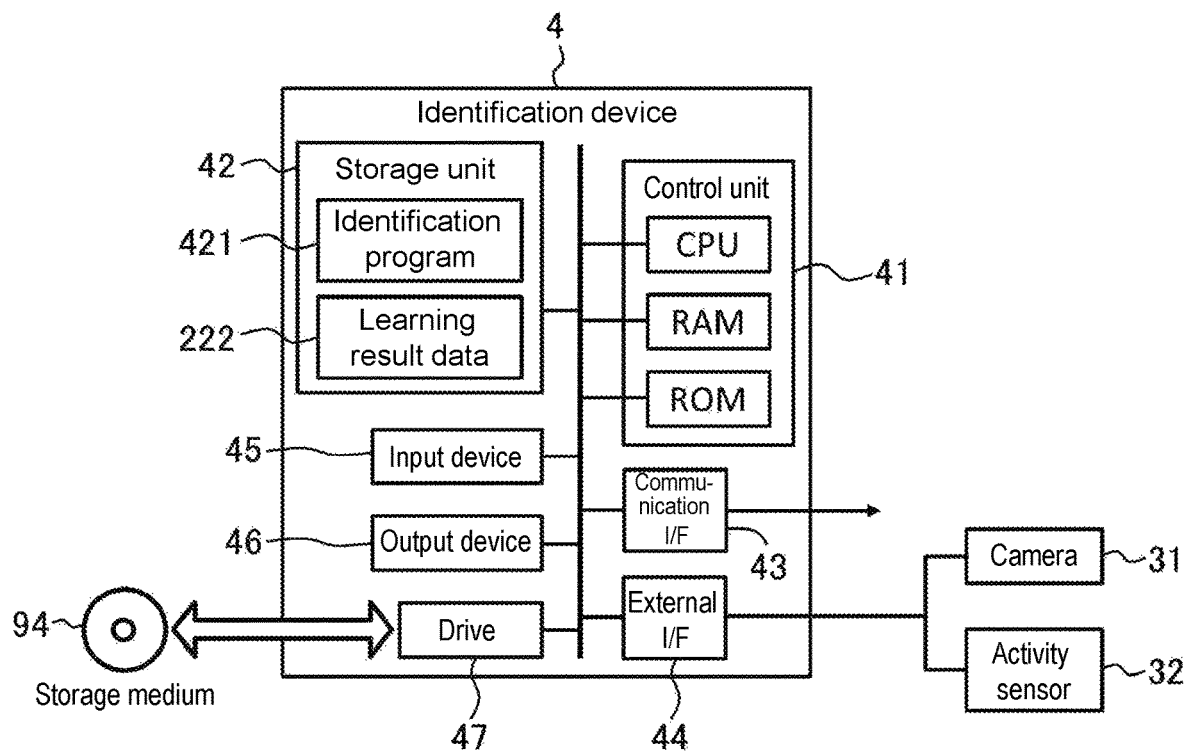
FIG. 4 schematically illustrates an example of the hardware configuration of an identification device according to an embodiment.

Next, an example of the hardware configuration of the identification device 4 according to the present embodiment is described with reference to FIG. 4. FIG. 4 schematically illustrates an example of the hardware configuration of the identification device 4 according to the present embodiment.

As shown in FIG. 4, the identification device 4 according to the present embodiment is a computer in which a control unit 41, a storage unit 42, a communication interface 43, an external interface 44, an input device 45, an output device 46, and a drive 47 are electrically connected. Moreover, similar to FIG. 2, the communication interface and the external interface in FIG. 4 are described as "communication I/F" and "external I/F".

The control unit 41 to the drive 47, and the storage medium 94 have the same configuration as the control unit 11 to the drive 17 of the annotation device 1, and the storage medium 91, respectively. The control unit 41 includes a CPU serving as a hardware processor, a RAM, a ROM, and the like, and is configured to execute various information processing based on programs and data. The storage unit 42 includes, for example, a hard disk drive, a solid state drive, or the like, and stores a variety of information such as an identification program 421 and the learning result data 222. The identification program 421 is a program for causing the identification device 4 to execute the information processing (FIG. 18) described later for estimating the behavioral state of the worker by using the trained learner constructed by the learning device 2, and includes a series of commands of the information processing. The details are described later.

The communication interface 43 is, for example, a wired LAN module, a wireless LAN module, or the like, and is used to perform data communication with the annotation device 1 and the learning device 2 via a network. The external interface 44 is, for example, a USB port, a dedicated port, or the like, and is used to connect to the camera 31 and the activity sensor 32. The input device 45 is a device for inputting, such as a mouse, a keyboard, or the like. In addition, the output device 46 is a device for outputting, such as a display, a speaker, or the like. The user can operate the identification device 4 via the input device 45 and the output device 46.

The drive 47 is, for example, a CD drive, a DVD drive, or the like, and is used for reading a program stored in the storage medium 94. The type of the drive 47 may be appropriately selected according to the type of the storage medium 94. At least one of the identification program 421 and the learning result data 222 may be stored in the storage medium 94. The storage medium 94 is a medium for storing information, such as a program, by electrical, magnetic, optical, mechanical, or chemical action so that the recorded information such as a program can be read by a computer or other devices, machines, or the like. The identification device 4 may acquire at least one of the identification program 421 and the learning result data 222 from the storage medium 94. Here, similar to FIGS. 2 and 3, a disc type storage medium such as a CD, a DVD, or the like is illustrated as an example of the storage medium 94 in FIG. 4. However, similar to the above, the type of the storage medium 94 is not limited to the disc type and may be other types.

Moreover, regarding the specific hardware configuration of the identification device 4, similar to the annotation device 1 and the learning device 2, constituent components can be omitted, replaced, and added as appropriate according to the embodiment. In addition, the identification device 4 may be a general-purpose server device, PC, or the like, in addition to the information processing device designed specifically for the service to provide.

Software Configuration

<Annotation Device>

Figure 5:
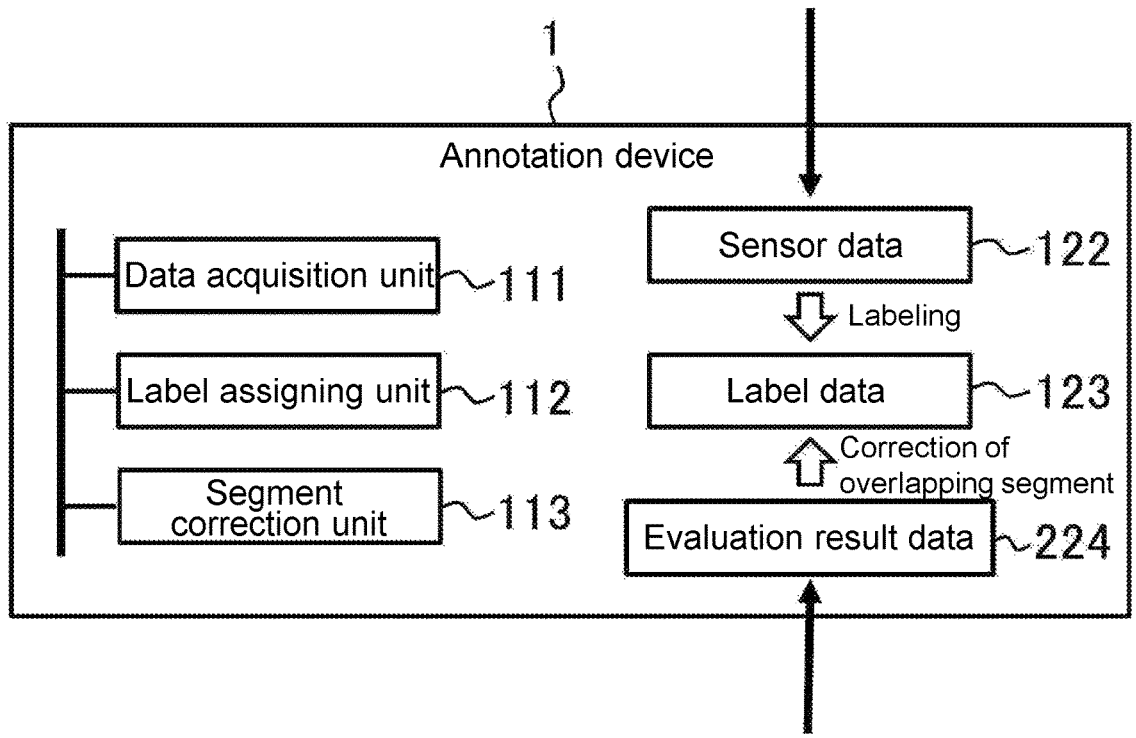
FIG. 5 schematically illustrates an example of the software configuration of the annotation device according to the embodiment.

Next, an example of the software configuration of the annotation device 1 according to the present embodiment is described with reference to FIG. 5. FIG. 5 schematically illustrates an example of the software configuration of the annotation device 1 according to the present embodiment.

The control unit 11 of the annotation device 1 expands, in the RAM, an annotation program 121 stored in the storage unit 12. Then, the control unit 11 interprets and executes the annotation program 121 expanded in the RAM by the CPU to control each constituent component. Thus, as shown in FIG. 5, the annotation device 1 according to the present embodiment is configured as a computer including a data acquisition unit 111, a label assignment unit 112, and a segment correction unit 113 as software modules. That is, in the present embodiment, each software module is implemented by the control unit 11 (CPU).

The data acquisition unit 111 acquires the sensor data 122 in which the outputs of the sensor (the camera 31 and the activity sensor 32 in the present embodiment) are arranged in time series. The label assignment unit 112 assigns a plurality of labels to the acquired sensor data 122. At this time, the label assignment unit 112 arranges an overlapping segment between two labelled time segments consecutive in the time series (time axis) in at least a part of the sensor data 122, the two consecutive labelled time segments partially overlapping each other in the time series (time axis) in the overlapping segment.

Specifically, the plurality of the assigned labels include the first label 1231 and the second label 1232. The label assignment unit 112 sets the first time segment assigned with the first label 1231, and the second time segment right after the first time segment in the time series and assigned with the second label 1232 as follows.

That is, when setting each time segment to which each label is assigned in the sensor data 122, the label assignment unit 112 sets the start time of the first time segment to be earlier than the start time of the second time segment, and sets the end time of the first time segment to be earlier than the end time of the second time segment. On the other hand, the label assignment unit 112 sets the end time of the first time segment to be later than the start time of the second time segment. Accordingly, the label assignment unit 112 sets the first time segment and the second time segment so as to arrange an overlapping segment between the first time segment and the second time segment that are adjacent to each other, in which the first time segment and the second time segment partially overlap each other in the time series in the overlapping segment. The label assignment unit 112 stores the result of the labelling performed as above as the label data 123.

Moreover, the content of each label assigned to each time segment may be appropriately determined according to the embodiment. In the present embodiment, the label assignment unit 112 sets the content of each label so as to indicate the correct answer of the predetermined inference on the sensor data 122 in the time segment assigned with each label. Therefore, each label may also be referred to as "teacher data" or "correct answer data".

In the present embodiment, because the sensor data 122 is obtained from the camera 31 and the activity sensor 32 which are configured to monitor the state of the factory worker, the label assignment unit 112 can set the content of each label so as to indicate the behavioral state of the worker in the labelled time segment. Accordingly, the label assignment unit 112 can generate the labelled sensor data 124 that can be used for supervised learning which is configured to enable the learner to acquire the ability to estimate the behavioral state of the worker based on the data obtained from the camera and the activity sensor, as an example of the predetermined inference.

The segment correction unit 113 acquires the evaluation result data 224 indicating the evaluation result on the trained learner which is constructed to have the ability of performing a predetermined inference. Then, the segment correction unit 113 changes the time width of the overlapping segment based on the evaluation result indicated by the acquired evaluation result data. When the time width of the overlapping segment is changed, the segment correction unit 113 reflects the changed content in the label data 123.

Learning Device

Figure 6:
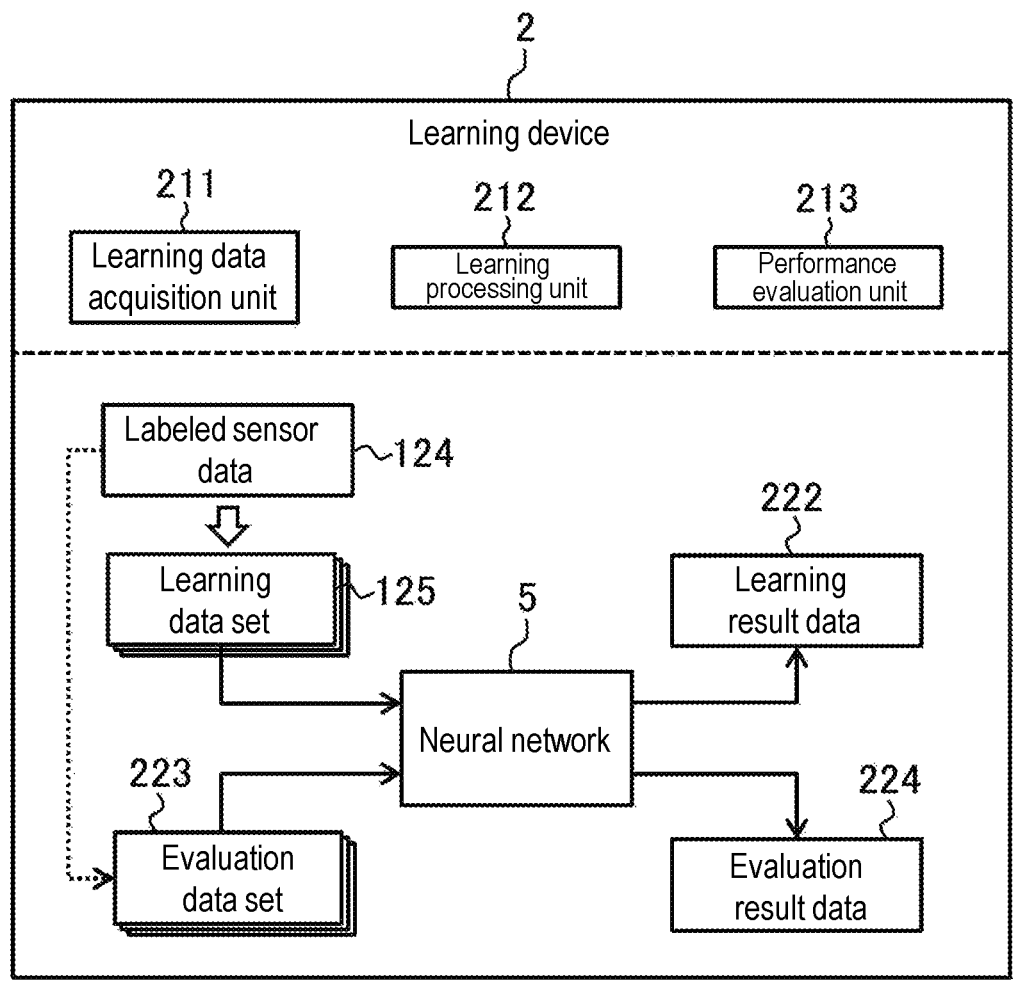
FIG. 6 schematically illustrates an example of the software configuration of the learning device according to the embodiment.

Next, an example of the software configuration of the learning device 2 according to the present embodiment is described with reference to FIG. 6. FIG. 6 schematically illustrates an example of the software configuration of the learning device 2 according to the present embodiment.

The control unit 21 of the learning device 2 expands, in the RAM, the learning program 221 stored in the storage unit 22. Then, the control unit 21 interprets and executes the learning program 221 expanded in the RAM by the CPU to control each constituent component. Thus, as shown in FIG. 6, the learning device 2 according to the present embodiment is configured as a computer including a learning data acquisition unit 211, a learning processing unit 212, and a performance evaluation unit 213 as software modules. That is, in the present embodiment, each software module is implemented by the control unit 21 (CPU).

The learning data acquisition unit 211 acquires a learning data set 125 used for machine learning. The learning processing unit 212 uses the learning data set 125 to perform supervised learning of a neural network 5. Accordingly, the learning processing unit 212 constructs a trained neural network 5 that has acquired the ability to perform a predetermined inference. The neural network 5 is an example of the "learner". The performance evaluation unit 213 evaluates the performance of the constructed trained neural network 5 by using the evaluation data set 223, and stores the evaluation result as the evaluation result data 224.

Learning Process

Figure 7A:
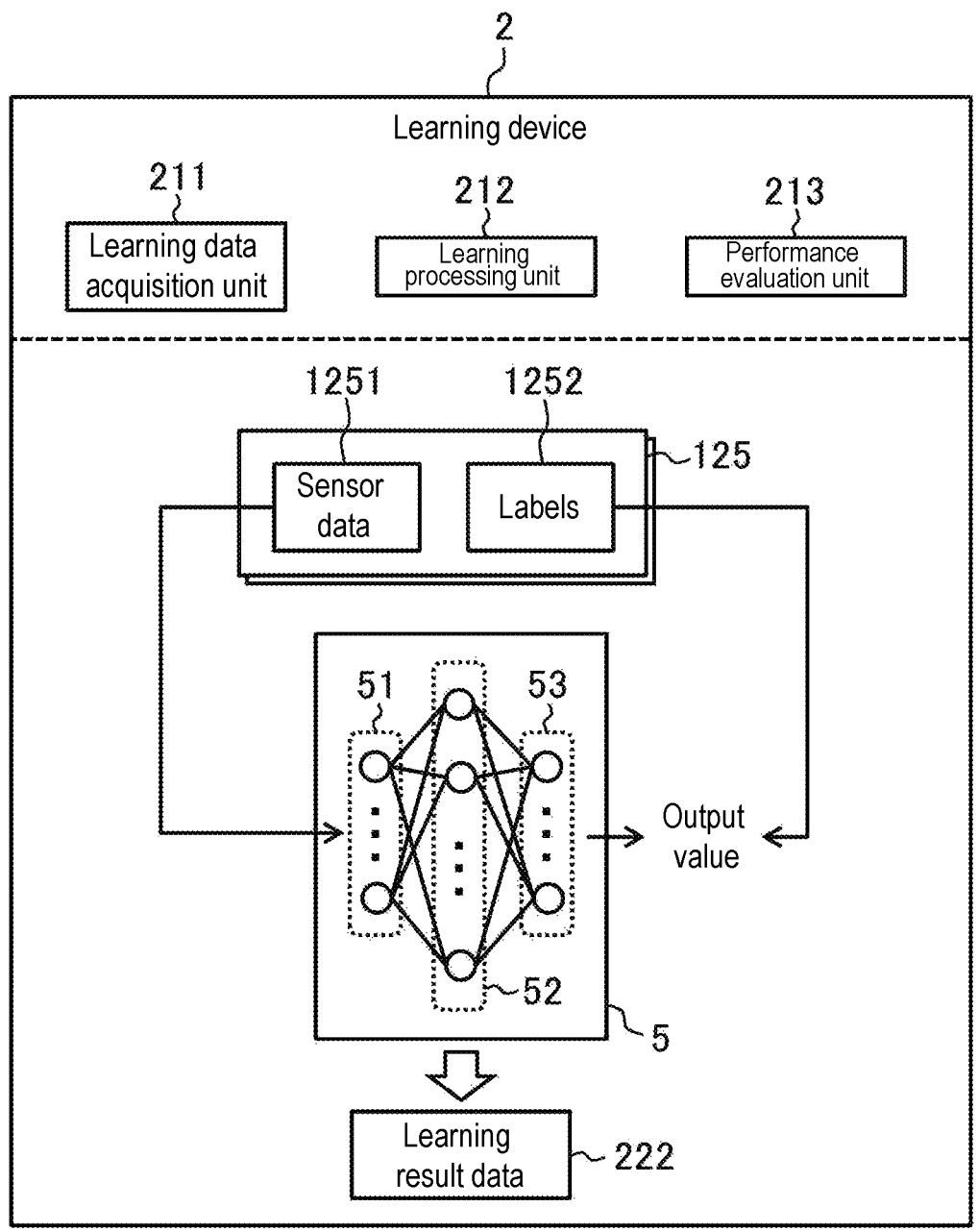
FIG. 7A schematically illustrates the process of machine learning of a learner performed by the learning device according to the embodiment.

Here, the process of supervised learning performed by the learning processing unit 212 is described with reference to FIG. 7A. FIG. 7A schematically illustrates the process of supervised learning of the neural network 5 performed by the learning processing unit 212 according to the present embodiment.

First, the learning data set 125 used for the supervised learning is described. The learning data set 125 is configured with pairs of sensor data 1251 and labels 1252 and is generated from the labelled sensor data 124. Specifically, the learning data set 125 can be generated by extracting the labelled sensor data 124 in units of the labelled time segment. That is, the sensor data 1251 is a part of the sensor data 122 specified in the target time segment, and the labels 1252 are labels assigned to the time segments.

Next, the neural network 5 serving as a learning model for acquiring the ability to perform a predetermined inference by supervised learning is described. The neural network 5 according to the present embodiment is a so-called multi-layered neural network and includes an input layer 51, an intermediate layer (hidden layer) 52, and an output layer 53 sequentially from the input side. However, the number of layers of the neural network 5 is not limited to the above example and may be appropriately selected according to the embodiment.

Each of the layers 51 to 53 includes one or more neurons (nodes). The number of the neurons included in each of the layers 51 to 53 may be appropriately set according to the embodiment. For example, the number of neurons in the input layer 51 may be appropriately set according to the sensor data 1251. In addition, the number of neurons in the output layer 51 may be set according to the number of types of the labels 1252.

The neurons in adjacent layers are appropriately connected to each other, and a weight (connection weight) is set for each connection. In the example of FIG. 7A, each neuron is connected to all neurons in the adjacent layer. However, the connection of the neurons is not limited to the above example and may be appropriately set according to the embodiment.

A threshold value is set for each neuron, and basically, the output of each neuron is determined by whether the sum of products of each input and each weight exceeds the threshold value. When the sensor data 1251 of each learning data set 125 is input to the input layer 51, the learning processing unit 212 constructs the neural network 5 that outputs the value corresponding to the label 1252 associated with the input sensor data 1251 from the output layer 53. The learning processing unit 212 then stores the configuration of the constructed neural network 5 (for example, the number of layers of the neural network, the number of the neurons in each layer, the connection relationship between the neurons, and the transfer function of each neuron), the connection weights between the neurons, and information indicating the threshold value of each neuron as the learning result data 222 in the storage unit 22.

Evaluation Process

Figure 7B:
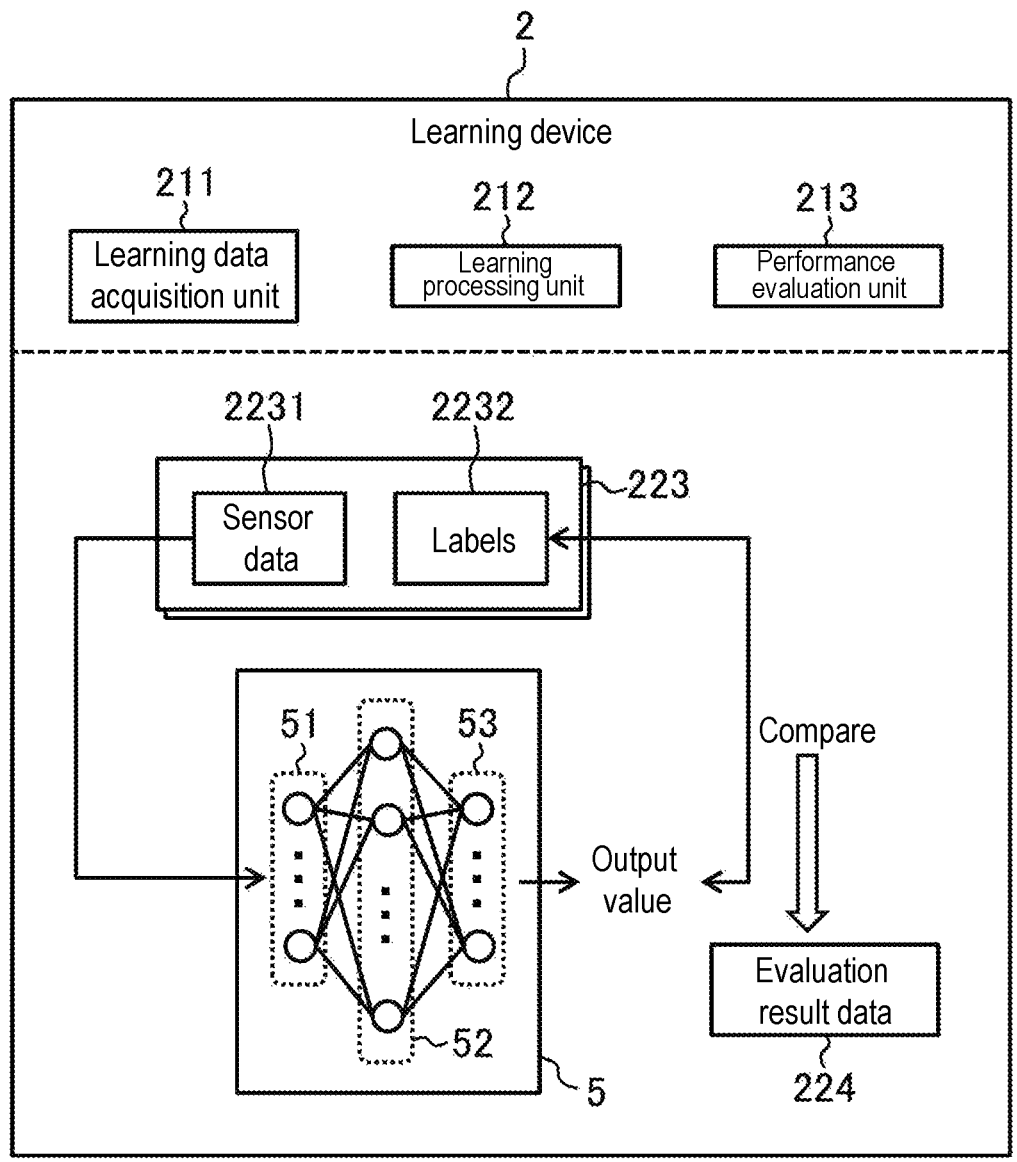
FIG. 7B schematically illustrates the process of a performance evaluation of a trained learner performed by the learning device according to the embodiment.

Next, the process of evaluating the performance of the trained neural network 5 by the performance evaluation unit 213 is described with reference to FIG. 7B. FIG. 7B schematically illustrates the process of evaluating the performance of the trained neural network 5 by the performance evaluation unit 213 according to the present embodiment.

The evaluation data set 223 is used for the performance evaluation on the trained neural network 5. Similar to the learning data set 125, the evaluation data set 223 is configured with pairs of sensor data 2231 and labels 2232. The sensor data 2231 of the evaluation data set 223 is an example of the "other sensor data different from the sensor data" of the present invention.

The evaluation data set 223 may be appropriately generated according to the embodiment. For example, the evaluation data set 223 may be generated from a portion other than the portion used as the learning data set 125 among the labelled sensor data 124. In this case, the evaluation data set 223 can be generated by the same method as the learning data set 125. In addition, for example, the evaluation data set 223 can be generated by the operator appropriately labelling the sensor data obtained from the camera and the activity sensor.

The performance evaluation unit 213 inputs the sensor data 2231 of the evaluation data set 223 to the input layer 51 of the trained neural network 5 and executes the arithmetic processing of the trained neural network 5 to obtain an output value from the output layer 53. The output value indicates the result of performing a predetermined inference on the sensor data 2231 by the trained neural network 5.

Therefore, the performance evaluation unit 213 compares the obtained output value with the label 2232 associated with the input sensor data 2231 to determine whether the predetermined inference on the sensor data 2231 performed by the trained neural network 5 is correct. Accordingly, the performance evaluation unit 213 according to the present embodiment can obtain an evaluation result represented by a correct answer rate at a time when the predetermined inference is performed on the sensor data 2231 by the trained neural network 5. The performance evaluation unit 213 stores the obtained evaluation result information as the evaluation result data 224 in the storage unit 22.

Moreover, the correct answer rate is the ratio of the evaluation data set 223 for which the predetermined inference performed by the trained neural network 5 is correct in the evaluation data set 223 used for evaluation. On the contrary, the ratio of the evaluation data set 223 for which the predetermined inference performed by the trained neural network 5 is incorrect in the evaluation data set 223 used for evaluation can be referred to as "incorrect answer rate". The incorrect answer rate is inextricably linked to the correct answer rate. Therefore, in the present embodiment, expression of the evaluation result by the incorrect answer rate is the same as expression of the evaluation result by the correct answer rate.

Identification Device

Figure 8:
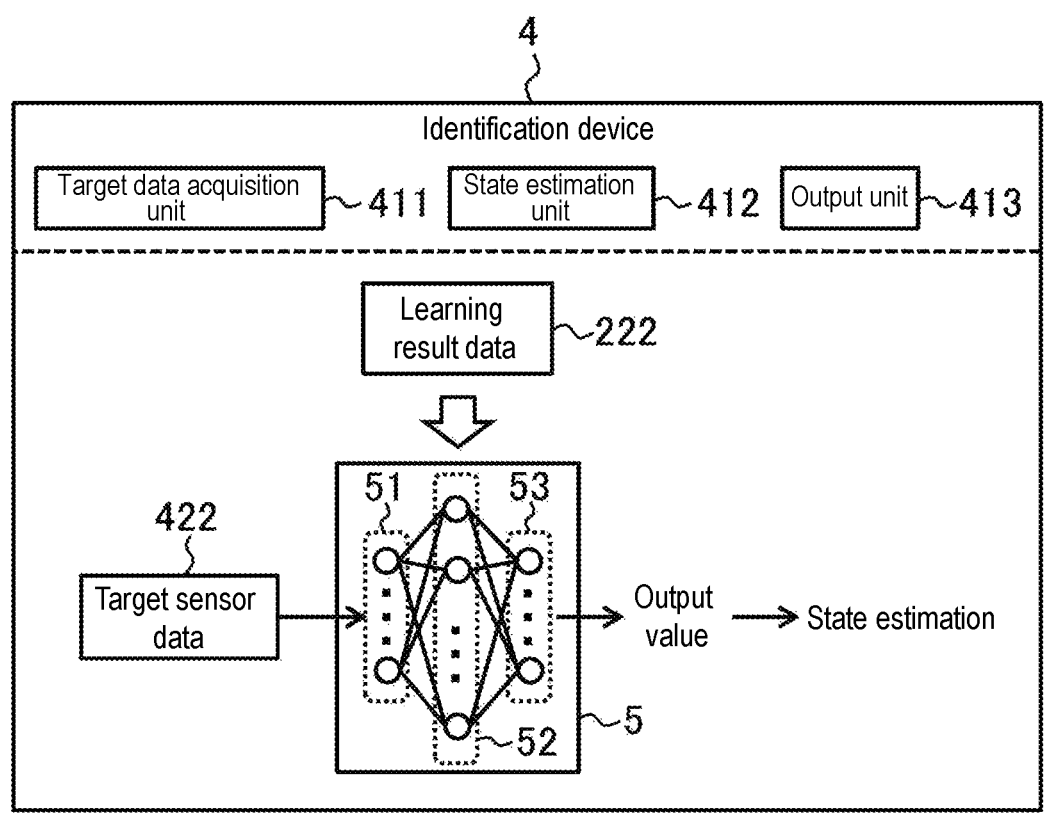
FIG. 8 schematically illustrates an example of the software configuration of the identification device according to the embodiment.

Next, an example of the software configuration of the identification device 4 according to the present embodiment is described with reference to FIG. 8. FIG. 8 schematically illustrates an example of the software configuration of the identification device 4 according to the present embodiment.

The control unit 41 of the identification device 4 expands, in the RAM, the identification program 421 stored in the storage unit 42. Then, the control unit 41 interprets and executes the identification program 421 expanded in the RAM by the CPU to control each constituent component. Accordingly, as shown in FIG. 8, the identification device 4 according to the present embodiment is configured as a computer including a target data acquisition unit 411, a state estimation unit 412, and an output unit 413 as software modules.

The target data acquisition unit 411 acquires target sensor data 422 serving as a target from which the behavioral state of the worker is estimated. The state estimation unit 412 includes the trained neural network 5. Specifically, the state estimation unit 412 sets the trained neural network 5 used for estimating the behavioral state of the worker by referring to the learning result data 222. Subsequently, the state estimation unit 412 inputs the target sensor data 422 to the trained neural network 5 and executes the arithmetic processing of the trained neural network 5 to obtain an output value from the trained neural network 5. Then, the state estimation unit 412 estimates the behavioral state of the worker indicated by the target sensor data 422 based on the output value obtained from the trained neural network 5. The output unit 413 outputs the result of estimating the behavior state of the worker by the state estimation unit 412.

Others

Details of the software modules of the annotation device 1, the learning device 2, and the identification device 4 are described in operation examples described later. Moreover, in the present embodiment, an example is described in which each software module of the annotation device 1, the learning device 2, and the identification device 4 is implemented by a general-purpose CPU. However, some or all of the above software modules may be implemented by one or more dedicated processors. In addition, regarding the software configurations of the annotation device 1, the learning device 2, and the identification device 4, the software modules may be omitted, replaced, and added as appropriate according to the embodiment.

§ 3 Operation Example

[Annotation Processing]

Figure 9:
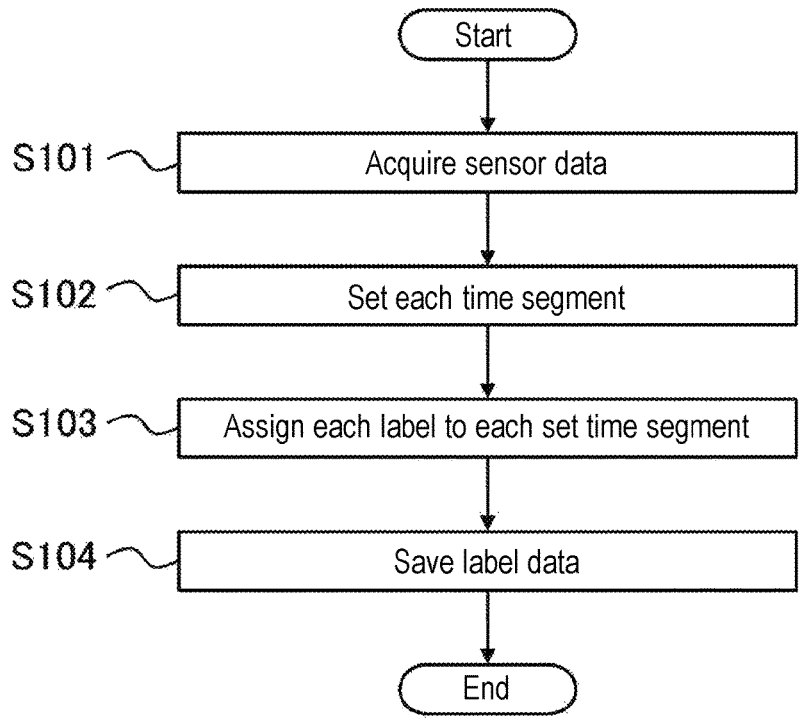
FIG. 9 illustrates an example of a processing procedure of the annotation device according to the embodiment.

Next, the annotation processing performed by the annotation device 1 is described with reference to FIG. 9. FIG. 9 is a flowchart illustrating an example of the procedure of the annotation processing performed by the annotation device 1. Moreover, the processing procedure described below is an example of the "annotation method" of the present invention. However, the processing procedure described below is merely an example, and each processing may be changed as much as possible. In addition, in the processing procedure described below, the steps may be omitted, replaced, and added as appropriate according to the embodiment.

(Step S101)

In step S101, the control unit 11 operates as the data acquisition unit 111 and acquires the sensor data 122 in which the outputs of the sensor are arranged in time series. When the sensor data 122 is acquired, the processing proceeds to the next step S102.

In the present embodiment, the camera 31 and the activity sensor 32 are connected to the annotation device 1 as sensors. Therefore, the control unit 11 may directly acquire the sensor data 122 from the camera 31 and the activity sensor 32. In addition, the control unit 11 may acquire the sensor data 122 not directly from the sensor but indirectly via another information processing device, storage medium, or the like. The process of acquiring the sensor data 122 may be appropriately determined according to the embodiment.

In addition, the sensor data 122 may be the output signal of the sensor, or may be data obtained by applying some information processing to the output signal of the sensor. The content of the sensor data is not particularly limited as long as labelling is possible. In the present embodiment, the control unit 11 can acquire image data and numerical data as the sensor data 122 from the camera 31 and the activity sensor 32.

(Steps S102 and S103)

In step S102, the control unit 11 operates as the label assignment unit 112 and sets a plurality of time segments in the acquired sensor data 122. In the next step S103, the control unit 11 assigns one or more labels to the set time segments. Accordingly, the control unit 11 assigns a plurality of labels to the sensor data 122.

Figure 10:
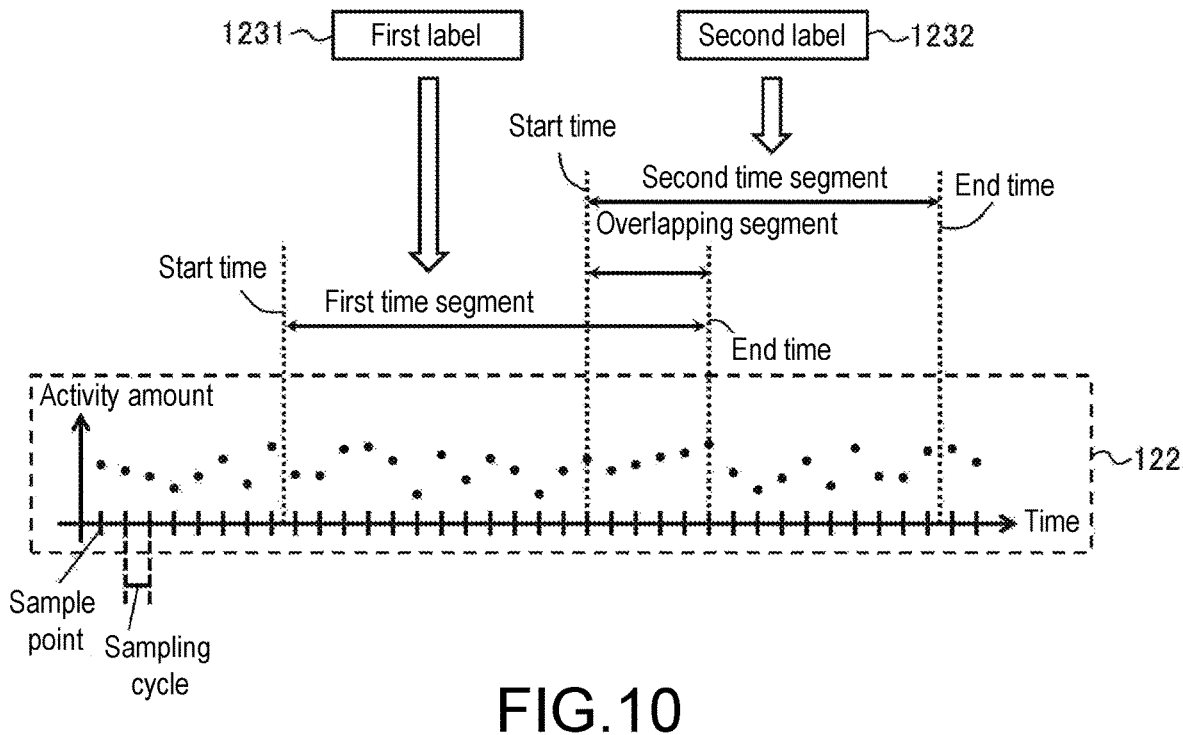
FIG. 10 schematically illustrates a relationship between a first time segment assigned with a first label and a second time segment assigned with a second label.

Here, the method of assigning the label is described with reference to FIG. 10. FIG. 10 schematically illustrates the relationship between the first time segment assigned with the first label 1231 and the second time segment assigned with the second label 1232. In the present embodiment, the control unit 11 assigns a plurality of labels including the first label 1231 and the second label 1232 to at least a part of the sensor data 122, so that an overlapping segment can be arranged between two time segments consecutive in the time series (time axis), in which the two time segments partially overlap each other in the time series (time axis) in the overlapping segment.

Specifically, the control unit 11 sets the first time segment assigned with the first label 1231, and the second time segment right after the first time segment in the time series and assigned with the second label 1232 as follows. That is, as illustrated in FIG. 10, when setting each time segment to which each label is assigned in the sensor data 122, the control unit 11 sets the start time of the first time segment to be earlier than the start time of the second time segment, and sets the end time of the first time segment to be earlier than the end time of the second time segment. On the other hand, the control unit 11 sets the end time of the first time segment to be later than the start time of the second time segment. Accordingly, the control unit 11 sets a time segment from the start time of the second time segment to the end time of the first time segment as an overlapping segment between the first time segment and the second time segment that are consecutive in the time series (time axis), in which the first time segment and the second time segment partially overlap each other in the time series in the overlapping segment.

The method of determining the start time and the end time of each time segment may be appropriately selected according to the embodiment. For example, the start time and the end time of each time segment may be designated by a user such as an operator via the input device 15. In addition, for example, the start time and the end time of each time segment may be determined by appropriately analyzing the sensor data 122, or may be determined based on the output of another sensor different from the sensor that obtained the sensor data 122. As an example, a scene in which a time segment assigned with a label indicating that the worker holds a target object is set is assumed. In this scene, the control unit 11 may determine the start time of the time segment by performing image analysis on the sensor data 122 (image data) obtained from the camera 31. In addition, the control unit 11 may determine the start time of the time segment based on the output of a pressure sensor attached to the target object.

When the start time and the end time of each time segment are determined first, the control unit 11 may set the determined start time of the second time segment as the start time of the overlapping segment and set the determined end time of the first time segment as the end time of the overlapping segment. On the other hand, when the range of the overlapping segment is determined first by the setting method described later, the control unit 11 may set the start time of the determined overlapping segment as the start time of the second time segment and set the end time of the determined overlapping segment as the end time of the first time segment.

Moreover, the expressions "first" and "second" merely indicate relative positional relationships in time series. In the example of FIG. 10, the first time segment assigned with the first label 1231 may be treated as the second time segment assigned with the second label based on the relationship with the time segment that is earlier than the first time segment in the time series. Similarly, the second time segment assigned with the second label 1232 may be treated as the first time segment assigned with the first label based on the relationship with the time segment that is later than the second time segment in the time series.

In addition, the time width of the overlapping segment may be appropriately determined according to the embodiment. For example, when the outputs of the sensor such as the camera 31 and the activity sensor 32 are subjected to digital signal processing, the sensor data 122 is obtained by sampling the outputs of the sensor at every sampling cycle, as illustrated in FIG. 10. In this case, the control unit 11 may set the time width of the overlapping segment based on the sampling cycle of the sensor so that the overlapping segment includes a plurality of sample points for sampling the outputs of the sensor respectively. That is, the control unit 11 may set the time width of the overlapping segment to be twice or more the sampling cycle. This prevents the overlapping segment from being set to contain substantially only one time point and ensures that the boundary between the first time segment and the second time segment can have a temporal width. In the example of FIG. 10, the control unit 11 sets the overlapping segment so as to include six sample points.

In addition, the method of setting the overlapping segment (that is, determining the range of the overlapping segment) may be appropriately selected according to the embodiment. For example, the control unit 11 may determine the range of the overlapping segment by receiving the input of the start time and the end time of the overlapping segment from the operator. In the present embodiment, the range of the overlapping segment can be determined by the following three methods.

(A-1) First Method

Figure 11A:
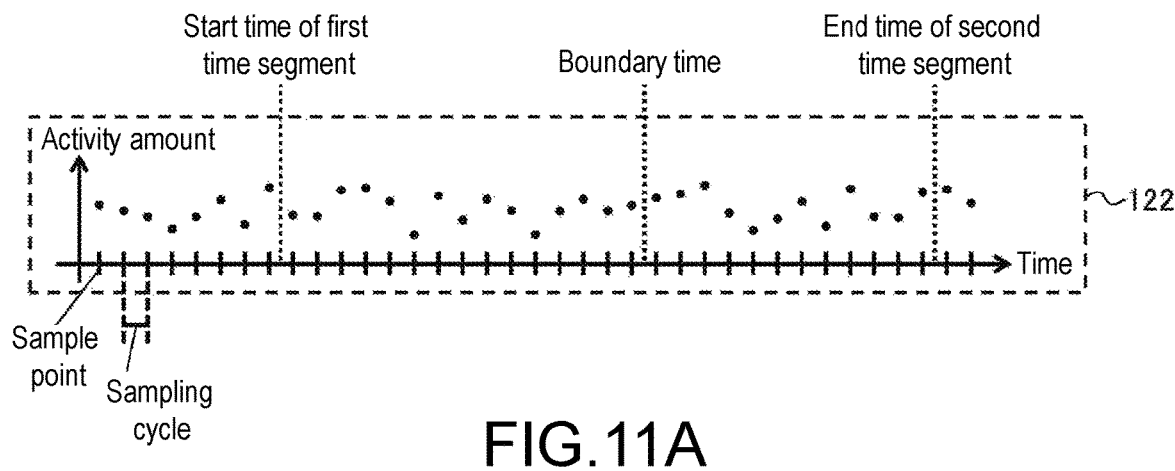
FIG. 11A schematically illustrates the process of a first method for setting an overlapping segment.
Figure 11B:
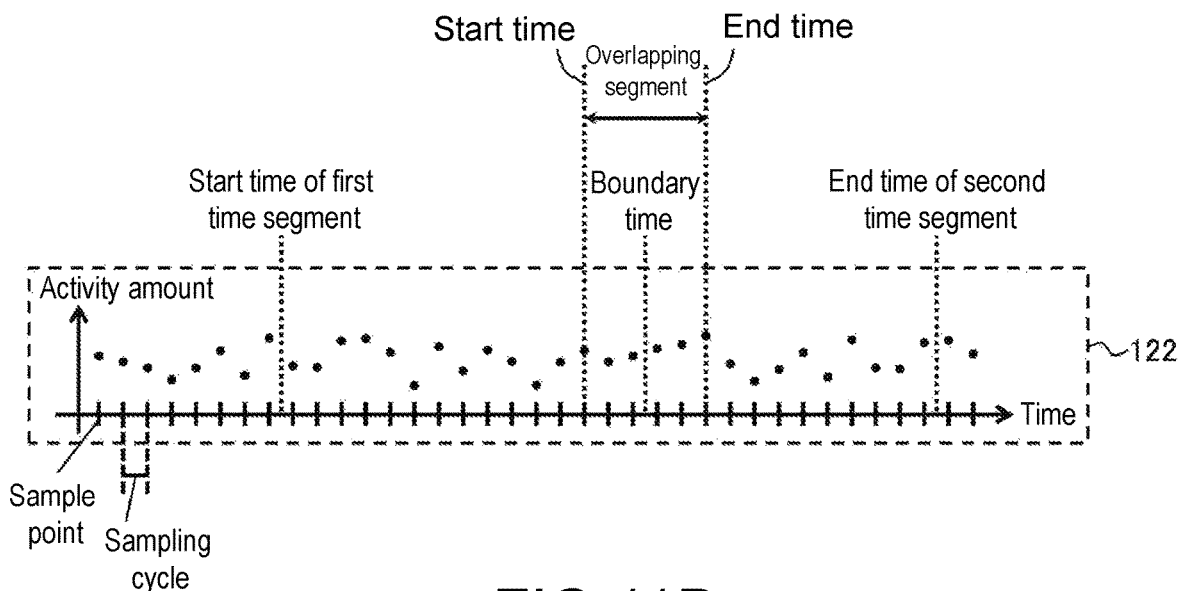
FIG. 11B schematically illustrates the process of the first method for setting the overlapping segment.
Figure 11C:
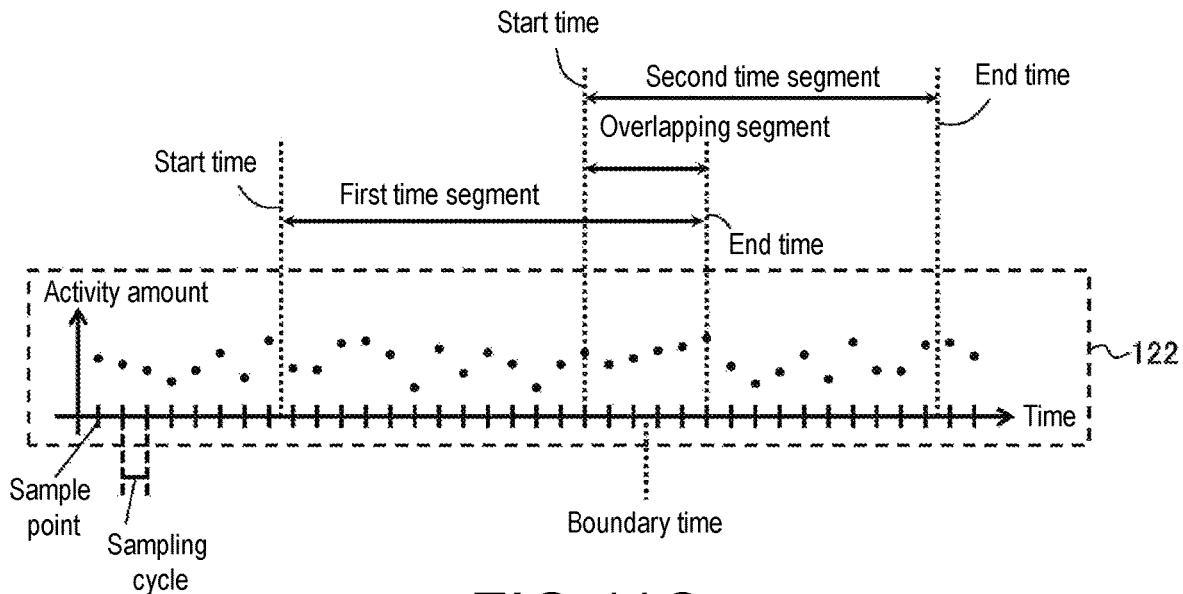
FIG. 11C schematically illustrates the process of the first method for setting the overlapping segment.

First, a first method for setting the overlapping segment is described with reference to FIGS. 11A to 11C. FIGS. 11A to 11C schematically illustrate the process of the first method for setting the overlapping segment. In the first method, the control unit 11 determines the range of the overlapping segment based on a provisional boundary time.

Specifically, as illustrated in FIG. 11A, the control unit 11 sets a boundary time that provisionally divides the first time segment and the second time segment between the start time of the first time segment and the end time of the second time segment. The method for setting the boundary time may be appropriately selected according to the embodiment. For example, the control unit 11 may receive designation of the time from the user via the input device 15 and set the designated time as the boundary time. The boundary time may be designated by inputting a numerical value or may be designated by designating a position in the timeline. In addition, for example, similar to the start time and the end time, the boundary time may be set by appropriately analyzing the sensor data 122, or may be set based on the output of another sensor different from the sensor that obtained the sensor data 122.

Subsequently, as illustrated in FIG. 11B, the control unit 11 sets an overlapping segment having a predetermined time width so as to include at least one time before or after the set provisional boundary time. Thereby, the control unit 11 can determine the range of the overlapping segment. Moreover, in the example of FIG. 11B, the control unit 11 sets the overlapping segment so as to include both times before and after the boundary time. However, the method of setting the overlapping segment based on the boundary time may not be limited to the above example, and the control unit 11 may set the overlapping segment so as to include only one of the times before and after the boundary time.

The predetermined time width of the overlapping segment may be appropriately determined according to the embodiment. For example, the predetermined time width may be a fixed value. The fixed value may be given in the annotation program 121 in advance, or may be given by the input of a user such as an operator. In this case, the control unit 11 may set, in the sensor data 122, an overlapping segment having a time width of the given fixed value based on the provisional boundary time. Accordingly, the amount of calculation required to set the overlapping segment in step S102 can be reduced.

In addition, for example, the predetermined time width may be determined based on the type of at least one of the first label 1231 and the second label 1232. In this case, the annotation device 1 may hold the correspondence information indicating the correspondence relationship between the label type and the set time width value in the storage unit 12. Then, the control unit 11 may refer to the correspondence information and set, based on the provisional boundary time, an overlapping segment having a time width of a value corresponding to the type of at least one of the first label 1231 assigned to the first time segment and the second label 1232 assigned to the second time segment. Accordingly, the time width of the overlapping segment can be appropriately set based on the type of label to be assigned, and thus desired information can be added to the sensor data 122 more accurately.

Moreover, the specific value of the time width of the overlapping segment corresponding to the label type may be appropriately determined according to the embodiment. For example, in the present embodiment, a scene in which the actions of "visually recognizing", "holding", "transporting" and "adjusting" taken by the factory worker are monitored by the camera 31 and the activity sensor 32 is assumed. In this case, compared with the transition from the "holding" state to the "transporting" state, the time required for the transition from the "visually recognizing" state to the "holding" state is usually longer. Consequently, in the above correspondence information, the value of the time width corresponding to "visual recognizing" and "holding" may be set to be larger than the value of the time width corresponding to "holding" and "transporting".

Finally, as shown in FIG. 11C, the control unit 11 sets the end time of the overlapping segment as the end time of the first time segment, and sets the range between the start time of the first time segment and the end time of the overlapping segment as the range of the first time segment. Additionally, the control unit 11 sets the start time of the overlapping segment as the start time of the second time segment, and sets the range between the start time of the overlapping segment and the end time of the second time segment as the range of the second time segment. Accordingly, the control unit 11 can set the first time segment and the second time segment in such a manner that an overlapping segment is arranged between the first time segment and the second time segment.

Moreover, the start time of the first time segment and the end time of the second time segment may be appropriately determined as described above. In addition, when the first time segment shown in FIGS. 11A to 11C is treated as the second time segment based on the relationship with the time segment earlier than the first time segment, the control unit 11 may set the start time of the overlapping segment which is set based on the relationship with the earlier time segment as the start time of the first time segment. Similarly, when the second time segment shown in FIGS. 11A to 11C is treated as the first time segment based on the relationship with the time segment later than the second time segment, the control unit 11 may set the end time of the overlapping segment which is set based on the relationship with the later time segment as the end time of the second time segment. The same applies to the following second and third methods.

(A-2) Second Method

Figure 12:
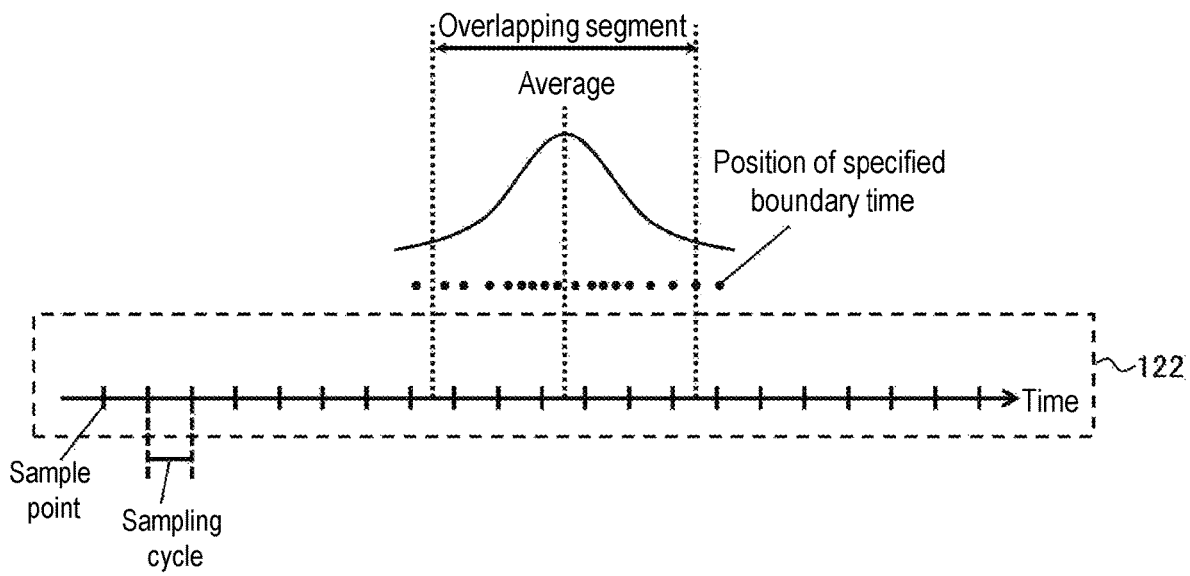
FIG. 12 schematically illustrates an example of a second method for setting the overlapping segment.

Next, a second method for setting the overlapping segment is described with reference to FIG. 12. FIG. 12 schematically illustrates an example of the second method for setting the overlapping segment. In the second method, the range of the overlapping segment is determined by using a plurality of designated fluctuations concerning the boundary time.

Specifically, the control unit 11 receives a plurality of designations concerning the boundary time that provisionally divides the first time segment and the second time segment. Similar to the first method, the control unit 11 may receive the designation of the boundary time from the user via the input device 15. In addition, the boundary time may be designated by inputting a numerical value, or may be designated by designating a position in the timeline. At this time, the control unit 11 may receive a plurality of designations of the boundary time from one user, or may receive only one designation from one user. The method of receiving a plurality of designations of the boundary time may be appropriately determined according to the embodiment.

Subsequently, the control unit 11 calculates at least any one of the average and the variation of the boundary times given by the plurality of designations, and sets the overlapping segment based on at least any one of the calculated average and variation. The variation may be given by variance, standard deviation, and the like. For example, the control unit 11 may set the calculated average time of the boundary times as the reference of the overlapping segment (for example, the central time). In addition, the control unit 11 may set a value that is n times (n is an arbitrary number) the calculated variance or the standard deviation as the time width of the overlapping segment. Thereby, the range of the overlapping segment can be determined based on the average and the variation of the boundary times given by the plurality of designations. After determining the range of the overlapping segment, the control unit 11 can determine the range of each of the first time segment and the second time segment by the same method as the first method. According to the second method, the overlapping segment can be appropriately set by using the plurality of designated fluctuations concerning the boundary time, and thus desired information can be added to the sensor data 122 more accurately.

Moreover, when either the average or the variation is not used, the attribute of the overlapping segment specified by the value of the party that is not used may be appropriately determined. For example, when the average is not used, the control unit 11 sets any one of the boundary times given by the plurality of designations as the reference of the overlapping segment (for example, the central time, the start time, the end time, etc.). In addition, for example, when the variation is not used, the control unit 11 may determine the value of the time width of the overlapping segment by the same method as the first method.

(A-3) Third Method

Figure 13:
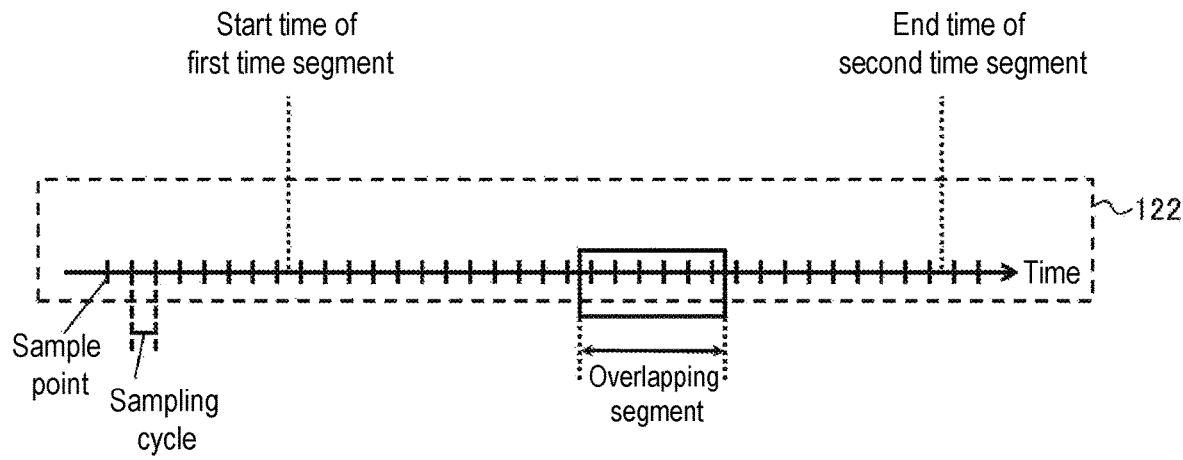
FIG. 13 schematically illustrates an example of a third method for setting the overlapping segment.

Next, a third method for setting the overlapping segment is described with reference to FIG. 13. FIG. 13 schematically illustrates an example of the third method for setting the overlapping segment. In the third method, the designation of the range of the overlapping segment is directly received.

Specifically, the control unit 11 receives designation of the segment in which the first time segment and the second time segment overlap. Then, the control unit 11 sets the designated segment as the overlapping segment. After setting the overlapping segment, the control unit 11 can determine the range of each of the first time segment and the second time segment by the same method as the first method. According to the third method, the overlapping segment can be set easily, and thus the amount of calculation required for the processing of step S102 can be reduced.

Moreover, the method of receiving the designation of the overlapping segment may be appropriately determined according to the embodiment. For example, the control unit 11 may output a timeline for displaying the range of each of the first time segment and the second time segment to the output device 16 (for example, a display), and receive, on the timeline, the designation of the segment in which the first time segment and the second time segment overlap. In this case, a user such as an operator can specify the range of the overlapping segment on the timeline by operating the input device 15.

(B) Content of Label

Next, the content of the label to be assigned is described. The content of the label to be assigned may be appropriately determined according to the embodiment. In the present embodiment, the control unit 11 sets the content of each label so as to indicate the correct answer of the predetermined inference on the sensor data 122 in the time segment to which each label is assigned. Specifically, the sensor data 122 is obtained from the camera 31 and the activity sensor 32 which are configured to monitor the state of the factory worker. Therefore, the control unit 11 may set the content of each label so as to indicate the behavioral state of the worker represented in each corresponding time segment. Accordingly, the labelled sensor data 124 available for supervised learning can be generated, and the supervised learning is configured to enable the learner to acquire the ability to perform the predetermined inference. One example of the predetermined inference is the ability to estimate the behavioral state of the worker based on the data obtained from the camera and the activity sensor.

Moreover, the method for determining the content of the label may be appropriately selected according to the embodiment. For example, the control unit 11 may output to the output device 16 (for example, a display) a list of candidates of the label to be assigned and receive selection of the labels to be assigned to each time segment. In this case, the user can operate the input device 15 to select a desired label from the list and thereby determine the content of the label to be assigned to the target time segment. In addition, for example, the content of the label may be determined by appropriately analyzing the corresponding time segment portion of the sensor data 122, or may be determined based on the output of another sensor different from the sensor that obtained the sensor data 122. For example, the control unit 11 may determine the content of the label assigned to the sensor data 122 by using an identifier that has acquired the ability to determine the content of the label from the sensor data by machine learning.

In addition, the data format of the label may be appropriately determined according to the embodiment. The content of the label may be designated by, for example, at least any one of a numerical value, a text, an image, and a voice. As a specific example, each time segment of the sensor data 122 may be labelled with a text indicating a behavioral state such as "visually recognizing", "holding", "transporting", or "adjusting" of the factory worker. In addition, as another specific example, each time segment of the sensor data 122 may be labelled with a numerical value indicating the visual field direction (an angle) of the factory worker, the position of the hand, the position of the target object, and the like.

In addition, a label different from the first label 1231 and the second label 1232 may be assigned to the overlapping segment. For example, a label indicating the transition from the state indicated by the first label 1231 to the state indicated by the second label 1232 may be assigned to the overlapping segment. Besides, for example, when the content of the label is specified by a numerical value, the overlapping segment may be labelled with one or more values indicating a transition from the value of the first label 1231 to the value of the second label 1232.

Figure 14:
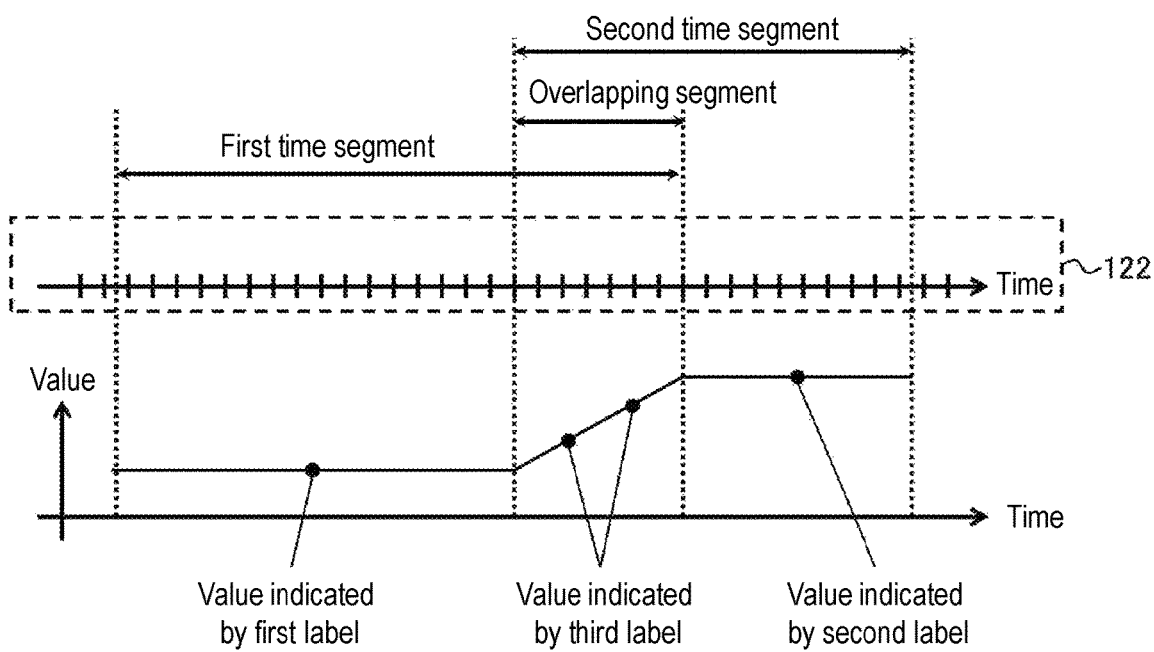
FIG. 14 schematically illustrates an example of the content of labels set in the overlapping segment.

FIG. 14 schematically illustrates an example of the content of the label set in the overlapping segment. In this case, the control unit 11 assigns a first value as the first label 1231 to the segment from the start time of the first time segment to the start time of the second time segment. In addition, the control unit 11 assigns a second value as the second label 1232 to the segment from the end time of the first time segment to the end time of the second time segment. Then, the control unit 11 assigns one or more values as labels to the overlapping segment from the end time of the first time segment to the start time of the second time segment so as to transition from the first value to the second value.

The value of the label assigned to the overlapping segment is a value between the first value and the second value. As illustrated in FIG. 14, when the first value is smaller than the second value and a plurality of values are assigned to the overlapping segment as labels, the control unit 11 may select the plurality of values assigned to the overlapping segment in a manner that the values monotonically increase from the start time to the end time of the overlapping segment. On the other hand, when the first value is larger than the second value and a plurality of values are assigned to the overlapping segment as labels, the control unit 11 may select the plurality of values assigned to the overlapping segment in a manner that the values monotonically decrease from the start time to the end time of the overlapping segment.

(C) Others

As described above, the control unit 11 can set a plurality of time segments including the first time segment and the second time segment that partially overlap each other in the sensor data 122, and assign labels to the set time segments. When a plurality of labels are assigned to the sensor data 122, the control unit 11 advances the processing to the next step S104.

Figure 15:
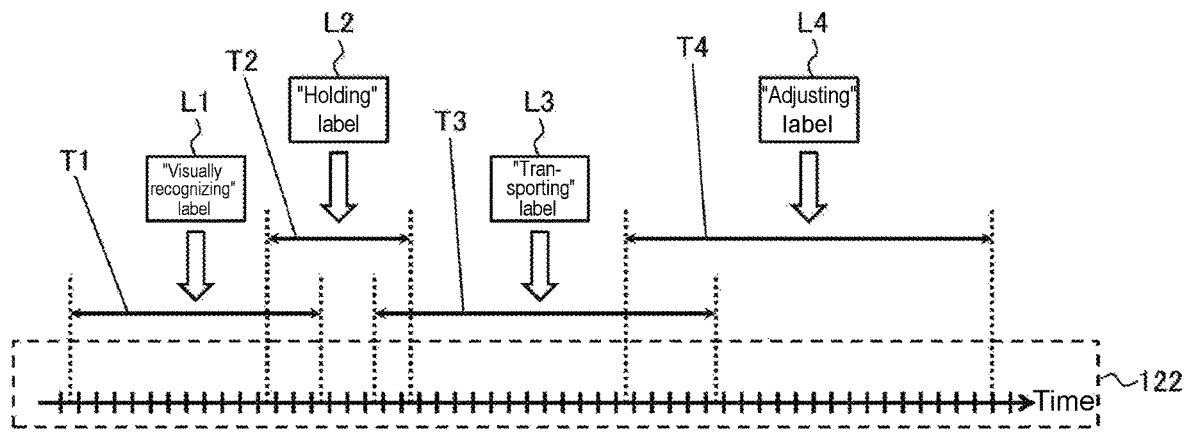
FIG. 15 schematically illustrates an example of an annotation for sensor data.

FIG. 15 schematically illustrates an example in which a label indicating the behavioral state of a factory worker is assigned to the sensor data 122 by the above processing. In the sensor data 122 illustrated in FIG. 15, four time segments T1 to T4 are set, and labels L1 to L4 (texts) indicating "visually recognizing", "holding", "transporting" and "adjusting" are assigned to the set time segments T1 to T4, respectively. "Visually recognizing" indicates a state in which the worker is visually checking the target object. "Holding" indicates a state in which the worker is holding the target object by hand. "Transporting" indicates a state in which the worker is carrying the target object by hand. "Adjusting" indicates a state in which the worker is taking other actions such as adjusting the position of the target object.

In the example of FIG. 15, in the relationship between the time segment T1 assigned with the label L1 of "visually recognizing" and the time segment T2 assigned with the label L2 of "holding", the time segment T1 corresponds to the first time segment, and the time segment T2 corresponds to the second time segment. The label L1 of "visually recognizing" corresponds to the first label 1231, and the label L2 of "holding" corresponds to the second label 1232. Similarly, in the relationship between the time segment T2 assigned with the label L2 of "holding" and the time segment T3 assigned with the label L3 of "transporting", the time segment T2 corresponds to the first time segment, and the time segment T3 corresponds to the second time segment. The label L2 of "holding" corresponds to the first label 1231, and the label L3 of "transporting" corresponds to the second label 1232. In addition, in the relationship between the time segment T3 assigned with the label L3 of "transporting" and the time segment T4 assigned with the label L4 of "adjusting", the time segment T3 corresponds to the first time segment and the time segment T4 corresponds to the second time segment. The label L3 of "transporting" corresponds to the first label 1231 and the label L4 of "adjusting" corresponds to the second label 1232.

In addition, in the example of FIG. 15, the time width of each overlapping segment set between two time segments (T1, T2), (T2, T3), and (T3, T4) consecutive in the time series (time axis) is determined according to the type of the label assigned to each time segment. Specifically, it is assumed that compared with the transition from the "holding" state to the "transporting" state, the time required for the transition from the "visually recognizing" state to the "holding" state is usually longer. Consequently, in the example of FIG. 15, the time width of the overlapping segment between the time segments (T1, T2) is set to be longer than the overlapping segment between the time segments (T2, T3). In addition, it is assumed that compared with the transition from the "holding" state to the "transporting" state, the time required for the transition from the "transporting" state to the "adjusting" state is usually longer. Consequently, in the example of FIG. 15, the time width of the overlapping segment between the time segments (T3, T4) is set to be longer than the overlapping segment between the time segments (T2, T3). As described above, when a plurality of overlapping segments are arranged in the time series, the time width of each overlapping segment may be determined to be different according to the types of at least two labels assigned to at least two time segments configuring each overlapping segment.

Moreover, in the example of FIG. 15, overlapping segments are arranged between a plurality of adjacent time segments of the sensor data 122. However, the portion in which the overlapping segment is set is not limited to the above example. The overlapping segment may also be arranged in at least a part of the plurality of adjacent time segments set in the sensor data 122. That is, the sensor data 122 may include a portion in which no overlapping segment is arranged between adjacent time segments. In the portion where no overlapping segment is arranged, the adjacent time segments may be separated by the boundary time as in the conventional way.

(Step S104)

In step S104, the control unit 11 operates as the label assignment unit 112 and stores the labelling result obtained from steps S102 and S103 as the label data 123 in the storage unit 12. Accordingly, the control unit 11 ends the annotation processing of this operation example, in other words, the generation processing of the labelled sensor data 124.

Moreover, the control unit 11 may transfer the generated labelled sensor data 124 to another information processing device such as a network attached storage (NAS) or the learning device 2 via a network at an optional timing after the processing of step S104 is completed. In addition, the control unit 11 may transfer the generated labelled sensor data 124 to the storage medium via the drive 17. Then, after the transfer is completed, the control unit 11 may delete the generated labelled sensor data 124 from the storage unit 12.

Learning Processing

Figure 16:
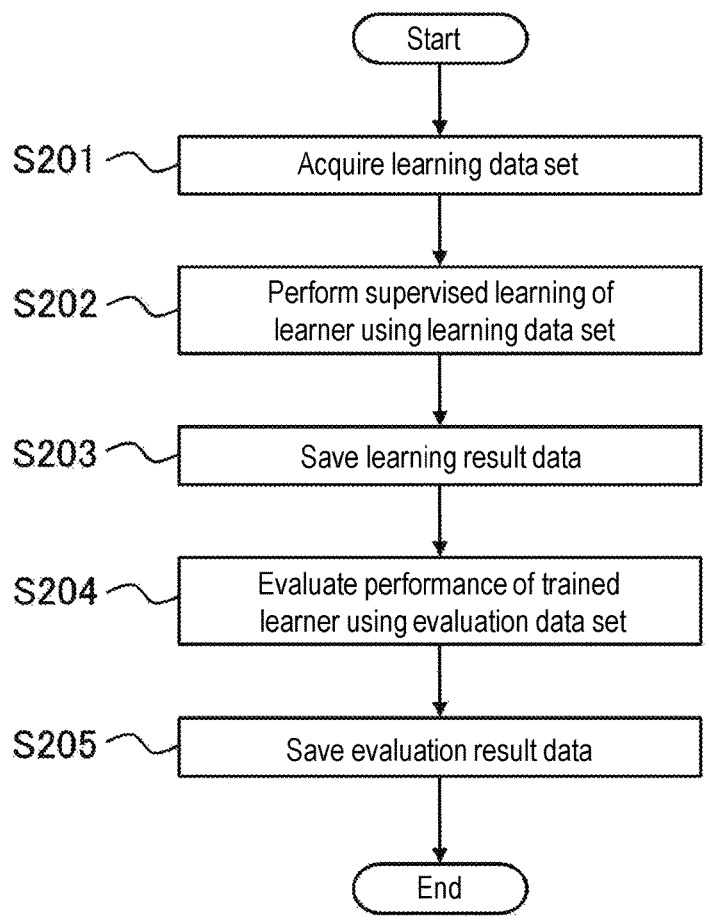
FIG. 16 illustrates an example of a processing procedure of the learning device according to the embodiment.

Next, an operation example of the learning device 2 is described with reference to FIG. 16. FIG. 16 is a flowchart illustrating an example of the processing procedure of the learning device 2. Moreover, the processing procedure described below is merely an example, and each processing may be changed as much as possible. In addition, in the processing procedure described below, steps can be omitted, replaced, and added as appropriate according to the embodiment.

(Step S201)

In step S201, the control unit 21 operates as the learning data acquisition unit 211 and acquires learning data set 125 used for the supervised learning of the neural network 5. The learning data set 125 is configured with pairs of sensor data 1251 and labels 1252 and is generated from the labelled sensor data 124.

The learning data set 125 may be acquired as appropriate. For example, the control unit 21 may acquire the labelled sensor data 124 from the annotation device 1, the NAS or the like via a network or from a storage medium via the drive 26. Then, the control unit 21 may generate the learning data set 125 by extracting the labelled sensor data 124 in units of the labelled time segments. Thereby, the control unit 21 can acquire the learning data set 125.

In addition, for example, the generation of the learning data set 125 may be performed by an information processing device other than the learning device 2. In this case, the control unit 21 can acquire the learning data set 125 generated by another information processing device via a network, a storage medium, or the like. The number of the acquired learning data sets 125 may be appropriately determined to a degree allowing the supervised learning of the neural network 5 to be performed. When the learning data set 125 is acquired, the control unit 21 advances the processing to the next step S202.

Moreover, when generating the learning data set 125 from the labelled sensor data 124, the processing of the overlapping segment may be appropriately determined according to the embodiment. For example, the part of the overlapping segment may be discarded. That is, the learning data set 125 corresponding to each segment may be generated by extracting a segment from the start time of the first time segment to the start time of the second time segment and a segment from the end time of the first time segment to the end time of the second time segment in the labelled sensor data 124.

In addition, for example, the part of the overlapping segment may be incorporated into both the first time segment and the second time segment. That is, the learning data set 125 corresponding to each segment may be generated by extracting the segment from the start time to the end time of the first time segment and the segment from the start time to the end time of the second time segment in the labelled sensor data 124.

In addition, for example, when a label different from the first label 1231 and the second label 1232 is assigned to the overlapping segment, the learning data set 125 corresponding to the overlapping segment may be generated by extracting the overlapping segment from the start time of the second time segment to the end time of the first time segment in the labelled sensor data 124. In this case, the learning data set 125 corresponding to each segment may be generated by extracting the segment from the start time of the first time segment to the start time of the second time segment and the segment from the end time of the first time segment to the end time of the second time segment in the labelled sensor data 124.

(Step S202)

In step S202, the control unit 21 operates as the learning processing unit 212 and uses the acquired learning data set 125 to perform the supervised learning of the neural network 5 so that the output value corresponding to the label 1252 is output when the sensor data 1251 is input.

Specifically, first, the control unit 21 prepares the neural network 5 to be subjected to the learning processing. The configuration of the prepared neural network 5, the initial value of the connection weight between the neurons, and the initial value of the threshold value of each neuron may be given by a template or may be given by the input from an operator. In addition, when re-learning is performed, the control unit 21 may prepare the neural network 5 based on the learning result data 222 that is subjected to re-learning.

Next, the control unit 21 uses the sensor data 1251 of the learning data set 125 acquired in step S201 as input data (training data) and uses the labels 1252 as teacher data (correct answer data) to perform the learning processing of the neural network 5. A known learning method such as a stochastic gradient descent method may be used for the learning processing of the neural network 5.

For example, the control unit 21 inputs the sensor data 1251 to the input layer 51 of the neural network 5. Then, the control unit 21 performs the firing determination of each neuron included in each of the layers 51 to 53 sequentially from the input side. Accordingly, the control unit 21 obtains the output value from the output layer 53 of the neural network 5. Next, the control unit 21 calculates an error between the output value obtained from the output layer 53 and the value corresponding to the label 1252. Subsequently, the control unit 21 uses the calculated error of the output value to calculate the error of the connection weights between the neurons and the error of the threshold values of the neurons by the back propagation method. Then, the control unit 21 updates the values of the connection weights between the neurons and the threshold values of the neurons based on the calculated errors.

For each learning data set 125, the control unit 21 repeats the series of processing until the output value output from the neural network 5 matches the value corresponding to the label 1252. Accordingly, the control unit 21 can construct the trained neural network 5 that outputs the output value corresponding to the label 1252 when the sensor data 1251 is input.

The supervised learning allows the neural network 5 to acquire the ability to perform a predetermined inference. In the present embodiment, in the annotation processing, the content of each label is set to indicate the behavioral state of the worker represented in each corresponding time segment. Therefore, by the processing of step S202, the trained neural network 5 that has acquired the ability to estimate the type of the behavioral state of the worker based on the data obtained from the camera and the activity sensor can be constructed. When the learning processing of the neural network 5 is completed, the control unit 21 advances the processing to the next step S203.

(Step S203)

In step S203, the control unit 21 operates as the learning processing unit 212, and stores the configuration of the constructed neural network 5, the connection weights between the neurons, and information indicating the threshold value of each neuron as the learning result data 222 in the storage unit 22. When the storage of the learning result data 222 is completed, the control unit 21 advances the processing to the next step S204.

(Step S204)

In step S204, the control unit 21 operates as the performance evaluation unit 213 and acquires the evaluation data set 223. Then, the control unit 21 uses the acquired evaluation data set 223 to evaluate the performance of the constructed trained neural network 5.

Similar to the learning data set 125, the evaluation data set 223 is configured with pairs of sensor data 2231 and labels 2232. The evaluation data set 223 may be appropriately generated according to the embodiment. For example, the evaluation data set 223 may be generated from a portion other than the portion used as the learning data set 125 among the labelled sensor data 124. In this case, the evaluation data set 223 can be generated by the same method as the learning data set 125.

In addition, for example, a camera and an activity sensor are prepared, and the factory worker is observed under various conditions by the prepared camera and activity sensor. Then, the evaluation data set 223 can be generated by assigning a label indicating the behavioral state of the factory worker to the obtained sensor data. At this time, the sensor data can be obtained by the same method as in step S101. In addition, the range of each time segment set in the sensor data can be determined by the same method as in step S102. Furthermore, the content of the label assigned to the sensor data can be determined by the same method as in step S103.

Moreover, the generation of the above-mentioned evaluation data set 223 may be performed by the learning device 2 or may be performed by an information processing device other than the learning device 2. For example, the control unit 21 may manually generate the evaluation data set 223 according to the operation of the input device 24 by an operator or the like, or may automatically generate the evaluation data set 223 according to the processing of the program. The control unit 21 can thereby acquire the evaluation data set 223. In addition, when the evaluation data set 223 is generated by another information processing device, the control unit 21 may acquire the evaluation data set 223 generated by the another information processing device via a network, a storage medium, or the like. Moreover, the number of the acquired evaluation data sets 223 may be appropriately determined to a degree allowing the performance of the neural network 5 to be evaluated.

Next, the control unit 21 inputs the sensor data 2231 of the acquired evaluation data set 223 to the input layer 51 of the trained neural network 5 constructed in step S202. Then, the control unit 21 performs the arithmetic processing of the trained neural network 5, in other words, the firing determination of each neuron included in each of the layers 51 to 53 sequentially from the input side. Accordingly, the control unit 21 obtains the output value from the output layer 53 of the trained neural network 5. The output value indicates the result of performing a predetermined inference on the sensor data 2231 by the trained neural network 5. In the present embodiment, the output value can indicate the result of estimating the behavioral state of the worker represented by the sensor data 2231.

Therefore, the control unit 21 compares the obtained output value with the label 2232 associated with the input sensor data 2231, that is, the label 2232 paired with the input sensor data 2231. Then, the control unit 21 determines, based on the comparison result, whether the predetermined inference on the sensor data 2231 performed by the trained neural network 5 is correct.

When the output value matches the value of the label 2232, the control unit 21 determines that the predetermined inference on the sensor data 2231 performed by the trained neural network 5 is correct. On the other hand, when the output value does not match the value of the label 2232, the control unit 21 determines that the predetermined inference on the sensor data 2231 performed by the trained neural network 5 is incorrect.

By performing the series of processing on all the acquired evaluation data sets 223, the control unit 21 can calculate, as an evaluation result, a correct answer rate at a time when a predetermined inference is performed on the sensor data 2231 by the learned neural network 5. After the evaluation result of the trained neural network 5 constructed to have the ability to perform a predetermined inference is obtained, the control unit 21 advances the processing to the next step S205.

(Step S205)

In step S205, the control unit 21 operates as the performance evaluation unit 213 and stores the evaluation result information obtained in step S204 as the evaluation result data 224 in the storage unit 22. Accordingly, the control unit 21 ends the processing procedure according to this operation example.

Moreover, the control unit 21 may transmit the learning result data 222 and the evaluation result data 224 generated by the above processing procedure to another information processing device at any timing. For example, the control unit 21 may transmit the generated learning result data 222 to another information processing device for estimating the behavioral state of the factory worker via a network, a storage medium, or the like. In the another information processing device, the trained neural network 5 that has acquired the ability to estimate the behavioral state of the worker based on the data obtained from the camera and the activity sensor is available by using the learning result data 222 obtained from the learning device 2. In addition, for example, the control unit 21 may transmit the generated evaluation result data 224 to the annotation device 1, the NAS or the like via a network, a storage medium or the like. The annotation device 1 can use the evaluation result data 224 for the following correction processing of the overlapping segment.

Correction of Overlapping Segment

Figure 17:
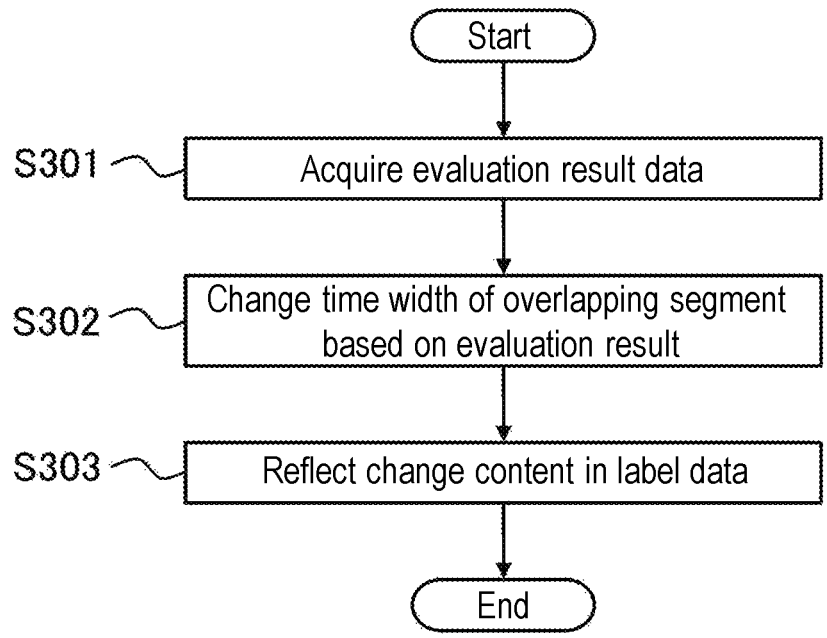
FIG. 17 illustrates an example of a processing procedure regarding correction of the overlapping segment of the annotation device according to the embodiment.

Next, processing of correcting the overlapping segment by the annotation device 1 is described with reference to FIG. 17. FIG. 17 is a flowchart illustrating an example of a processing procedure concerning the correction of the overlapping segment performed by the annotation device 1. Moreover, the processing procedure described below, including the annotation processing, is an example of the "annotation method" of the present invention. However, the processing procedure described below is merely an example, and each processing may be changed as much as possible. In addition, in the processing procedure described below, steps can be omitted, replaced, and added as appropriate according to the embodiment.

(Step S301)

In step S301, the control unit 11 operates as the segment correction unit 113 and acquires the evaluation result data 224. The evaluation result data 224 indicates the evaluation result of the trained neural network 5 constructed to have the ability to perform a predetermined inference by performing supervised learning using the labelled sensor data 124. The method for acquiring the evaluation result data 224 may be appropriately selected according to the embodiment. For example, the control unit 11 may acquire the evaluation result data 224 from the learning device 2, the NAS or the like via a network, a storage medium or the like. When the evaluation result data 224 is acquired, the control unit 11 advances the processing to the next step S302.

(Step S302)

In step S302, the control unit 11 operates as the segment correction unit 113 and changes the time width of the overlapping segment set in step S102 based on the evaluation result indicated by the acquired evaluation result data 224.

In the present embodiment, the evaluation result indicated by the evaluation result data 224 can be represented by the correct answer rate at the time when a predetermined inference is performed on the sensor data 2231 by the trained neural network 5. Therefore, the control unit 11 may change the time width of the overlapping segment by narrowing or expanding the time width of the overlapping segment when the correct answer rate indicated by the evaluation result data 224 is less than or equal to a predetermined threshold. Moreover, the method of changing the time width of the overlapping segment based on the evaluation result is not limited to the above example and may be appropriately determined according to the embodiment.

(Step S303)

In step S303, the control unit 11 operates as the segment correction unit 113 and reflects the change content in the label data 123 when the time width of the overlapping segment is changed in step S302. Accordingly, the control unit 11 ends the correction processing of the overlapping segment according to the present operation example.

Moreover, the control unit 11 may transmit the labelled sensor data 124 after the time width of the overlapping segment is changed to the learning device 2 via a network, a storage medium, or the like. The learning device 2 may perform the supervised learning of the neural network 5 again by using the learning data set 125 generated from the labelled sensor data 124 after the time width of the overlapping segment is changed. In addition, the learning device 2 may evaluate the reconstructed neural network 5 and regenerate the evaluation result data 224. Then, the control unit 11 may acquire the regenerated evaluation result data 224 and change the time width of the overlapping segment again. In this way, the learning processing and the evaluation processing of the neural network 5 performed by the learning device 2 and the correction processing of the overlapping segment performed by the annotation device 1 may be alternately and repeatedly executed.

In the process of executing this repetitive processing, the control unit 11 may appropriately determine whether to narrow or widen the time width of the overlapping segment in step S302. For example, when the processing of step S302 is executed first, the control unit 11 may select either to narrow or to widen the time width of the overlapping segment. In the processing of the second and subsequent times, the control unit 11 may appropriately determine whether to narrow or to widen the time width of the overlapping segment based on the change of the time width of the overlapping segment executed previously and the evaluation result obtained by a series of processing after the change. For example, it is assumed that the time width of the overlapping segment was narrowed in the processing of step S302 executed previously, and as a result, the evaluation result obtained by the series of processing after the change deteriorated (for example, the correct answer rate decreased). In this case, the control unit 11 may change the time width of the overlapping segment by expanding the time width of the overlapping segment. On the other hand, when the evaluation result becomes better (for example, the correct answer rate is enhanced), the control unit 11 may change the time width of the overlapping segment by further narrowing the time width of the overlapping segment.

Identification Processing

Figure 18:
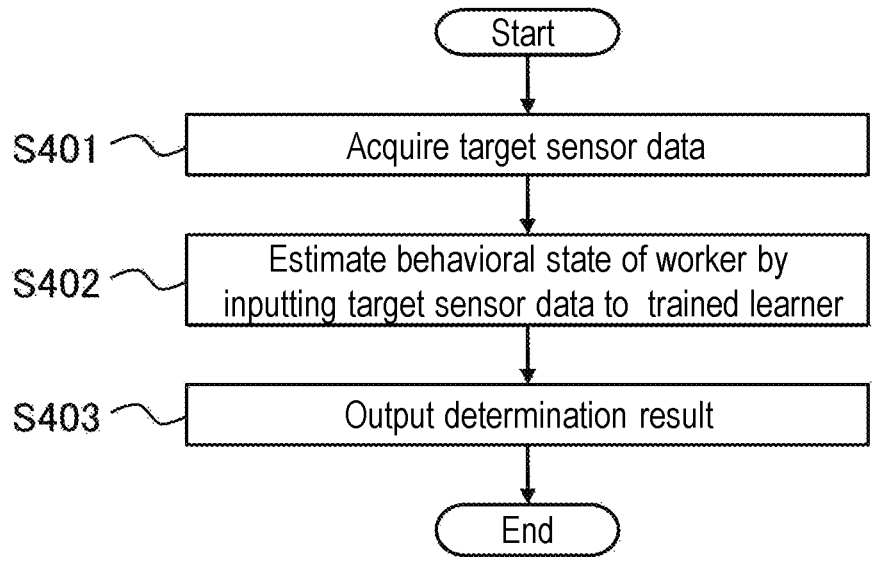
FIG. 18 illustrates an example of a processing procedure of the identification device according to the embodiment.

Next, processing of estimating the behavioral state of the worker by the identification device 4 is described with reference to FIG. 18. FIG. 18 is a flowchart illustrating an example of the processing procedure of the identification device 4 according to the present embodiment. Moreover, the processing procedure described below is merely an example, and each processing may be changed as much as possible. In addition, in the processing procedure described below, steps can be omitted, replaced, and added as appropriate according to the embodiment.

(Step S401)

In step S401, the control unit 41 operates as the target data acquisition unit 411 and acquires the target sensor data 422 serving as the target from which the behavioral state of the worker is estimated. When the target sensor data 422 is acquired, the processing proceeds to the next step S402.

In the present embodiment, the camera 31 and the activity sensor 32 are connected to the identification device 4 as sensors for monitoring the behavioral state of the worker. Consequently, the control unit 41 may directly acquire the target sensor data 422 from the camera 31 and the activity sensor 32. In addition, the control unit 41 may acquire the target sensor data 422 not directly from the sensor but indirectly via another information processing device, storage medium, or the like. The process of acquiring the target sensor data 422 may be appropriately determined according to the embodiment.

(Step S402)

In step S402, the control unit 41 operates as the state estimation unit 412 and sets the trained neural network 5 used for estimating the behavioral state of the worker by referring to the learning result data 222. Then, the control unit 41 inputs the target sensor data 422 to the trained neural network 5 and executes the arithmetic processing of the trained neural network 5. Accordingly, the control unit 41 acquires, from the trained neural network 5, the output value corresponding to the result of estimating the behavioral state of the worker represented by the target sensor data 422.

Specifically, the control unit 41 inputs the target sensor data 422 to the input layer 51 of the trained neural network 5 and performs the firing determination of each neuron included in each layer sequentially from the input side. Accordingly, the control unit 41 acquires, from the output layer 53 of the trained neural network 5, the output value corresponding to the result of estimating the behavioral state of the worker from the target sensor data 422.

Moreover, in the learning device 2, learning processing may be performed in a manner that the output value of the trained neural network 5 directly indicates the behavioral state of the worker. In this case, the control unit 41 can specify the behavioral state of the worker by obtaining the output value from the trained neural network 5. In addition, the identification device 4 may store, in the storage unit 42, reference information (not shown) in a table format or the like in which the output value of the trained neural network 5 and the behavioral state of the worker are associated with each other. In this case, the control unit 41 can specify the behavioral state of the worker corresponding to the output value obtained from the trained neural network 5 by referring to the reference information. Accordingly, when the behavioral state of the worker is estimated, the control unit 41 advances the processing to the next step S403.

(Step S403)

In step S403, the control unit 41 operates as the output unit 413 and outputs the result of estimating the behavioral state of the worker by step S402. Accordingly, the control unit 41 ends the processing procedure according to this operation example.

Moreover, the output method and the output content may be appropriately determined according to the embodiment. For example, the control unit 41 may store behavior information (not shown) indicating the ideal behavioral state of the worker in the storage unit 42. In this case, by comparing the result estimated by step S402 with the ideal behavioral state indicated by the behavior information, the control unit 41 may determine whether the behavioral state of the worker monitored by the camera 31 and the activity sensor 32 connected to the identification device 4 is ideal. Then, when the result estimated by step S402 does not match the ideal behavioral state indicated by the behavior information, that is, when the behavioral state of the worker is not ideal, the control unit 41 may output an instruction to correct the behavioral state via the output device 46 or the like. On the other hand, when the result estimated by step S402 matches the ideal behavioral state indicated by the behavior information, that is, when the behavioral state of the worker is ideal, the control unit 41 may perform an output for notifying the worker, a supervisor who supervises the worker, or the like, or may omit the output processing in step S403.

In addition, for example, the identification device 4 may estimate the behavioral states of a plurality of workers. In this case, the identification device 4 may determine whether there is a time segment in which the difference between the behavioral state of each worker estimated in step S402 and the ideal behavioral state indicated by the behavior information is larger than a threshold value. Then, when there is a time segment in which the difference between the behavioral state of each worker and the ideal behavioral state is larger than the threshold value, the control unit 41 may output an instruction to improve the process in the time segment via the output device 46 or the like. At this time, the control unit 41 may set the behavioral state that was the most frequent in the time segment as correct behavior, and output an instruction to perform the set correct behavior. In addition, the control unit 41 may output the position where the time segment exists in the work process. On the other hand, when such a time segment does not exist, the control unit 41 may omit the output processing in step S403.

Characteristics

As described above, the annotation device 1 according to the present embodiment arranges an overlapping segment between the first time segment assigned with the first label 1231 and the second time segment assigned with the second label 1232 by step S102, in which the first time segment and the second time segment partially overlap each other in the time series in the overlapping segment. Accordingly, the boundary between the first time segment and the second time segment can have a temporal width, and the timing of the transition from the state indicated by the first label 1231 to the state indicated by the second label 1232 can be prevented from being set to one point. That is, the transition from the state indicated by the first label 1231 to the state indicated by the second label 1232 can occur at any time in the overlapping segment, or the overlapping segment can represent the segment in which the transition occurs.

Therefore, according to the present embodiment, the overlapping segment arranged between the first time segment and the second time segment can appropriately represent the segment in which the transition from the state indicated by the first label 1231 to the state indicated by the second label 1232 occurs. Accordingly, compared with the conventional method in which the boundary of the time segment is determined at one point, desired information can be added to the sensor data 122 more accurately. In addition, in the learning device 2 in which the learning data set 125 generated from the obtained labelled sensor data 124 is used, a trained learner having a higher ability to estimate the type of the behavioral state of the worker based on the data obtained from the camera and the activity sensor can be constructed by the processing of steps S201 to S203.

In addition, in the present embodiment, the learning processing and the evaluation processing of the neural network 5 performed by the learning device 2 and the correction processing of the overlapping segment performed by the annotation device 1 can be alternately and repeatedly executed. In the process of executing the repetitive processing, the time width of the overlapping segment can be adjusted by the processing of step S302 so that the evaluation result on the trained neural network 5 becomes better. Therefore, according to the present embodiment, the labelled sensor data 124 capable of constructing the trained neural network 5 having an ability above a certain level to perform a predetermined inference can be generated. Accordingly, the identification device 4 in which the trained neural network 5 is used can perform a predetermined inference with a performance above a certain level. In the above embodiment, the identification device 4 can accurately estimate the behavioral state of the worker in step S402.

§ 4 Modification Example

Although the embodiments of the present invention have been described above in detail, the above description is merely an example of the present invention in all respects. It is evident that various improvements and modifications can be made without departing from the scope of the present invention. For example, the following changes are possible. Moreover, the same reference numerals are used for the same constituent components as those of the above embodiment, and description of the aspects similar to those of the above embodiment is appropriately omitted. The following modification examples can be combined as appropriate.

4.1

In the above embodiment, the identification system 100 is configured with three devices, namely the annotation device 1, the learning device 2, and the identification device 4. However, the configuration of the identification system 100 may not be limited to the above example. For example, the annotation device 1, the learning device 2, and the identification device 4 may be configured by an integrated computer. In addition, for example, two devices selected from the annotation device 1, the learning device 2, and the identification device 4 may be configured by an integrated computer.

4.2

In the above embodiment, the annotation device 1 labels (annotates) the sensor data 122 obtained from the camera 31 and the activity sensor 32 which monitor the state of the factory worker. However, the applicable scenes of the annotation device 1 are not limited to the above example.

In addition, in the above embodiment, the content of each label is set to indicate the correct answer of the predetermined inference on the sensor data 122 in each time segment to which the label is assigned. However, the content of each label is not limited to the above example and may be appropriately determined depending on the application scene of the annotation device 1.

Furthermore, in the above embodiment, the sensor data 122 is obtained from a sensor for monitoring the behavioral state of the worker. However, the target for which sensor data is acquired is not limited to the worker and may be, for example, a person other than the worker, or a target object other than person (for example, a machine such as a robot). Besides, the number of targets for which sensor data is acquired is not limited to one and may be two or more (for example, the target person and the target machine).

Figure 19:
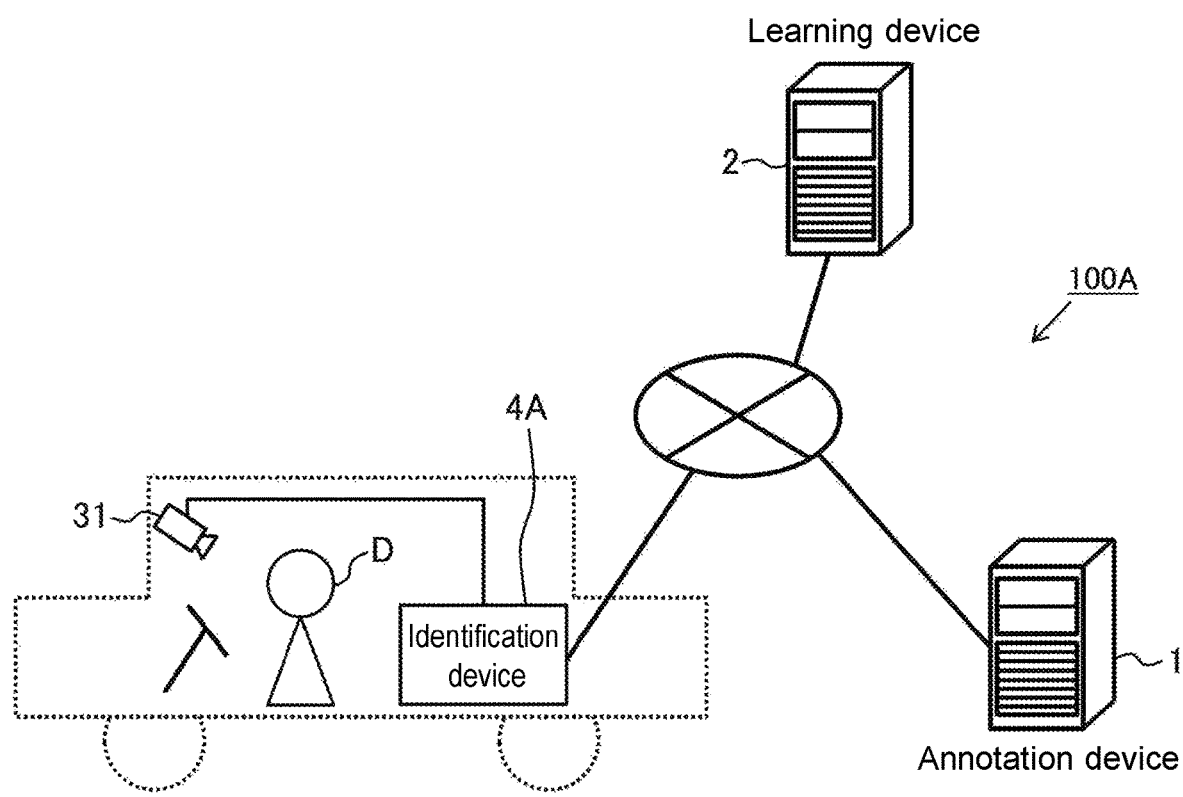
FIG. 19 schematically illustrates an example of another scene to which the present invention is applied.

FIG. 19 schematically illustrates an example of another scene to which the present invention is applied. FIG. 19 illustrates a scene in which the behavioral state of a driver D is estimated. An identification system 100A shown in FIG. 19 may be configured similarly to the identification system 100, except that the sensor data 122 according to the above embodiment is replaced with sensor data obtained from a sensor for monitoring the driver D. In addition, an identification device 4A may be configured similarly to the identification device 4 except that the identification device 4A is installed in a target vehicle. The trained neural network is, for example, configured to output an output value corresponding to the result of estimating the state of the driver D according to the target sensor data that is input. According to the identification system 100A, the state of the driver D in the vehicle can be monitored.

Moreover, the identification device 4A estimates the state of the driver D in step S402. Accordingly, the identification device 4A may control the vehicle according to the state of the driver D in step S403. For example, when it is estimated that the driver D driving the vehicle manually is in a state not suitable for driving, the identification device 4A may output a warning to stop the driving. In addition, in a case that an automatic driving mode that does not depend on the driving operation of the driver D can be implemented for the vehicle, when it is estimated that the driver D is in a state not suitable for driving, the identification device 4A may switch the operation mode of the vehicle from a manual driving mode to the automatic driving mode, or may prohibit switching from the automatic driving mode to the manual driving mode.

In addition, in the example of FIG. 19, as an example of a sensor for monitoring the driver D, the camera 31 is installed inside the vehicle. However, the sensor for monitoring the driver D is not limited to the camera and may be appropriately selected according to the embodiment. For example, as a sensor for monitoring the driver D, a biosensor such as a brain wave sensor or a pulse sensor may be used in addition to the activity sensor 32.

In addition, in the above embodiment and the example of FIG. 19, the present invention is applied to a scene in which the behavioral state of a person such as a factory worker or a car driver is estimated. However, the scene to which the present invention is applied is not limited to the scene in which the behavioral state of a person is estimated. The present invention can be applied to all scenes in which a predetermined inference is performed on the sensor data.

In this case, the annotation device 1 and the learning device 2 according to the above embodiments can be used directly by appropriately changing the contents of the sensor data 122 and the label data 123. That is, in step S103, the annotation device 1 sets the content of each label so as to indicate the correct answer of the predetermined inference on the sensor data in the time segment to which the label is assigned. In addition, in step S202, the learning device 2 constructs the trained learner that has acquired the ability to perform a predetermined inference such as identifying a feature included in the sensor data by performing supervised learning using the sensor data and a plurality of labels. Furthermore, the identification device 4 uses the trained learner constructed by the learning device 2 to perform the predetermined inference.

Figure 20:
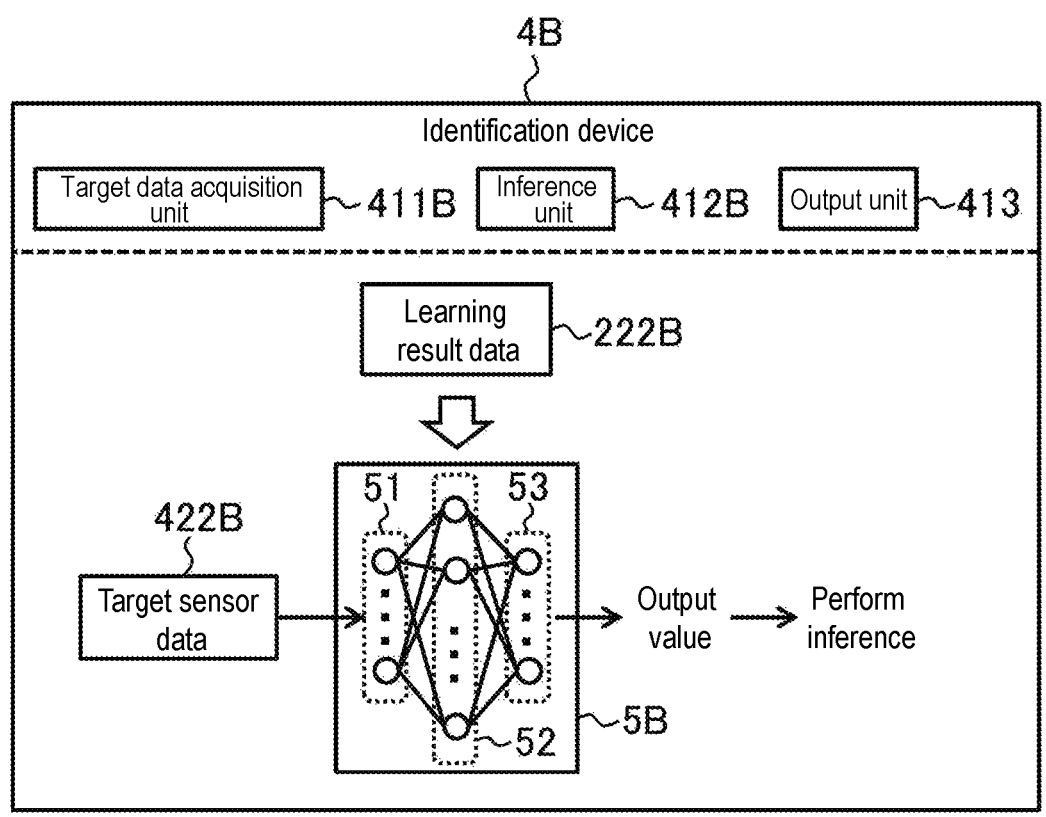
FIG. 20 schematically illustrates an example of the software configuration of an identification device according to another embodiment.

FIG. 20 schematically illustrates an example of the software configuration of an identification device 4B according to the present modification example. The hardware configuration and processing procedure of the identification device 4B may be the same as that of the identification device 4 according to the above embodiment. That is, in step S401, the control unit 41 of the identification device 4B operates as a target data acquisition unit 411B and acquires target sensor data 422B serving as the target to which a predetermined inference is performed. Then, in step S402, the control unit 41 sets a trained neural network 5B by referring to learning result data 222B. The learning result data 222B is generated by the learning device 2 performing the supervised learning for enabling the learner to acquire the ability to perform the predetermined inference. The control unit 41 inputs the target sensor data 422B into the trained neural network 5B and executes the arithmetic processing of the trained neural network 5B, thereby obtaining an output value corresponding to the result of performing the predetermined inference on the target sensor data 422B from the trained neural network 5B. Accordingly, the control unit 41 performs the predetermined inference on the target sensor data 422B. Then, in step S403, the control unit 41 operates as the output unit 413 and outputs the result of performing the predetermined inference. Moreover, the type of the inference to be performed may be appropriately determined according to the embodiment. For example, when the sensor data is voice data, the predetermined inference may be voice recognition.

4.3

In the above embodiment, as for the sensor data 122, the annotation device 1 processes the image data obtained from the camera 31 in the same manner as the numerical data obtained from the activity sensor 32. However, when multiple types of data are acquired as the sensor data 122, the processing of the various data may be different. For example, in the above steps S102 and S103, the control unit 11 may assign different labels to the image data obtained from the camera 31 and the numerical data obtained from the activity sensor 32.

4.4

In the above embodiment, the evaluation result indicated by the evaluation result data 224 can be represented by the correct answer rate at a time when the predetermined inference is performed on the sensor data 2231 by the trained neural network 5. However, the method of representing the evaluation result is not limited to the above example and may be appropriately determined according to the embodiment.

In addition, in the above embodiment, the evaluation result data 224 is generated by the learning device 2. However, the evaluation result data 224 may also be generated by another information processing device other than the learning device 2. That is, the learning processing (steps S201 to S203) and the evaluation processing (steps S204 and S205) of the neural network 5 may be executed by different computers.

4.5

In the above embodiment, a neural network (the neural network 5) is used as an example of the learner. However, the type of the learner that can be used in the above embodiment is not limited to the neural network. For example, in the above embodiment, a linear regression model, a support vector machine, or the like may be used as the learner.

What is claimed is:

1. An annotation method, in which a computer executes:
 a step of acquiring sensor data in which outputs of a sensor are arranged in time series; and
 a step of assigning a plurality of labels to the acquired sensor data, wherein
 the plurality of labels include a first label and a second label,
 the first label is assigned to a first time segment,
 the second label is assigned to a second time segment that comes after the first time segment in the time series,
 a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein
 the computer sets a boundary time that provisionally divides the first time segment and the second time segment, and
 sets the overlapping segment having a predetermined time width so as to include at least one time before or after the set boundary time, and wherein
 the predetermined time width is determined based on a type of at least one of the first label and the second label.

2. The annotation method according to claim 1, wherein the computer receives a designation of time from a user and sets the designated time as the boundary time.

3. The annotation method according to claim 1, wherein
 the computer receives a plurality of designations for a boundary time that provisionally divides the first time segment and the second time segment, and
 sets the overlapping segment based on at least any one of an average and a variation of the boundary times given by the plurality of designations.

4. The annotation method according to claim 1, wherein the computer receives a designation of a segment in which the first time segment and the second time segment overlap, and sets the designated segment as the overlapping segment.

5. The annotation method according to claim 1, wherein
 the computer assigns a first value as the first label to a segment from the start time of the first time segment to the start time of the second time segment,
 assigns a second value as the second label to a segment from the end time of the first time segment to the end time of the second time segment, and
 assigns one or more values as the labels of the overlapping segment to a segment from the end time of the first time segment to the start time of the second time segment so as to transition from the first value to the second value.

6. The annotation method according to claim 1, wherein each of the plurality of labels is set to indicate a correct answer of a predetermined inference on the sensor data in the time segment to which the label is assigned, and
the computer further executes:
a step of acquiring an evaluation result data indicating an evaluation result of a trained learner which is constructed to have an ability to perform the predetermined inference by performing supervised learning using the sensor data and the plurality of labels; and
a step of changing the time width of the overlapping segment based on the evaluation result indicated by the acquired evaluation result data.

7. The annotation method according to claim 6, wherein the evaluation result is represented by a correct answer rate at a time when the predetermined inference is performed on other sensor data different from the sensor data by the trained learner, and
when the correct answer rate indicated by the evaluation result data is less than or equal to a predetermined threshold, the computer changes the time width of the overlapping segment by narrowing or expanding the time width of the overlapping segment.

8. An annotation method, in which a computer executes:
a step of acquiring sensor data in which outputs of a sensor are arranged in time series; and
a step of assigning a plurality of labels to the acquired sensor data, wherein
the plurality of labels include a first label and a second label,
the first label is assigned to a first time segment,
the second label is assigned to a second time segment that comes after the first time segment in the time series,
a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein the computer sets a time width of the overlapping segment based on a sampling cycle of the sensor by including a plurality of sample points for sampling the output of the sensor respectively in the overlapping segment.

9. An annotation device, comprising:
a data acquisition unit for acquiring sensor data in which outputs of a sensor are arranged in time series; and
a label assignment unit for assigning a plurality of labels to the acquired sensor data, wherein
the plurality of labels include a first label and a second label,
the first label is assigned to the first time segment,
the second label is assigned to a second time segment that comes after the first time segment in the time series,
a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein
a boundary time that provisionally divides the first time segment and the second time segment is set, and
the overlapping segment having a predetermined time width is set so as to include at least one time before or after the set boundary time, and wherein
the predetermined time width is determined based on a type of at least one of the first label and the second label.

10. A non-transitory computer readable storage medium, storing an annotation program for causing a computer to execute:
a step of acquiring sensor data in which outputs of a sensor are arranged in time series; and
a step of assigning a plurality of labels to the acquired sensor data, wherein
the plurality of labels include a first label and a second label,
the first label is assigned to the first time segment,
the second label is assigned to a second time segment that comes after the first time segment in the time series,
a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein
a boundary time that provisionally divides the first time segment and the second time segment is set, and
the overlapping segment having a predetermined time width is set so as to include at least one time before or after the set boundary time, and wherein
the predetermined time width is determined based on a type of at least one of the first label and the second label.

11. An identification system, comprising:
a data acquisition unit for acquiring sensor data in which outputs of a sensor for monitoring a behavioral state of a factory worker are arranged in time series;
a label assignment unit for assigning a plurality of labels to the acquired sensor data, wherein each of the plurality of labels is set to indicate a correct answer of the behavioral state of the worker represented by the sensor data in a time segment to which the label is assigned;
a learning processing unit for constructing a trained learner to have an ability to estimate a type of the behavioral state of the worker by performing supervised learning using the sensor data and the plurality of labels;
a target data acquisition unit for acquiring target sensor data being a target from which the behavioral state of the worker is estimated;
a state estimation unit for estimating the behavioral state of the worker represented by the target sensor data by inputting the target sensor data to the trained learner and obtaining an output from the trained learner; and
an output unit for outputting the result of estimating the behavioral state of the worker, wherein
the plurality of labels include a first label and a second label,
the first label is assigned to the first time segment, the second label is assigned to a second time segment that comes after the first time segment in the time series, a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein a boundary time that provisionally divides the first time segment and the second time segment is set, and the overlapping segment having a predetermined time width is set so as to include at least one time before or after the set boundary time, and wherein the predetermined time width is determined based on a type of at least one of the first label and the second label.

12. An identification system, comprising:

a data acquisition unit for acquiring sensor data in which outputs of a sensor are arranged in time series;

a label assignment unit for assigning a plurality of labels to the acquired sensor data, wherein each of the plurality of labels is set to indicate a correct answer of a predetermined inference on the sensor data in a time segment to which the label is assigned;

a learning processing unit for constructing a trained learner to have an ability to perform the predetermined inference by performing supervised learning using the sensor data and the plurality of labels;

a target data acquisition unit for acquiring target sensor data being a target on which the predetermined inference is performed;

an inference unit for performing the predetermined inference on the target sensor data by inputting the target sensor data to the trained learner and obtaining an output from the trained learner; and an output unit for outputting a result of performing the predetermined inference, wherein the plurality of labels include a first label and a second label, the first label is assigned to the first time segment, the second label is assigned to a second time segment that comes after the first time segment in the time series, a start time of the first time segment is earlier than a start time of the second time segment, and an end time of the first time segment is earlier than an end time of the second time segment, whereas the end time of the first time segment is later than the start time of the second time segment, and thereby the first time segment and the second time segment are set to have an overlapping segment in which the first time segment and the second time segment partially overlap each other in the time series, wherein a boundary time that provisionally divides the first time segment and the second time segment is set, and the overlapping segment having a predetermined time width is set so as to include at least one time before or after the set boundary time, and wherein the predetermined time width is determined based on a type of at least one of the first label and the second label.

* * * * *